(12) United States Patent
Kitamura et al.

(10) Patent No.: US 9,586,972 B2
(45) Date of Patent: Mar. 7, 2017

(54) ORGANIC THIN FILM TRANSISTOR, ORGANIC SEMICONDUCTOR THIN FILM, AND ORGANIC SEMICONDUCTOR MATERIAL

(71) Applicant: FUJIFILM Corporation, Tokyo (JP)

(72) Inventors: Tetsu Kitamura, Ashigarakami-gun (JP); Koji Takaku, Ashigarakami-gun (JP); Wataru Sotoyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 67 days.

(21) Appl. No.: 14/632,669

(22) Filed: Feb. 26, 2015

(65) Prior Publication Data

US 2015/0166560 A1 Jun. 18, 2015

Related U.S. Application Data

(63) Continuation of application No. PCT/JP2013/071323, filed on Aug. 7, 2013.

(30) Foreign Application Priority Data

Aug. 27, 2012 (JP) .................................. 2012-187059

(51) Int. Cl.
*H01L 51/42* (2006.01)
*C07D 493/04* (2006.01)
(Continued)

(52) U.S. Cl.
CPC ........ *C07D 493/04* (2013.01); *H01L 51/0073* (2013.01); *H01L 51/0545* (2013.01);
(Continued)

(58) Field of Classification Search
CPC .............. C07D 493/04; H01L 51/0073; H01L 51/0545; H01L 51/0558; H01L 51/42; Y02E 10/549
See application file for complete search history.

(56) References Cited

U.S. PATENT DOCUMENTS 8,057,919 B2 11/2011 Kato et al.
8,138,355 B2 3/2012 Watanabe
(Continued)

FOREIGN PATENT DOCUMENTS

JP 2007-088222 A 4/2007
JP 2008-081494 A 4/2008
(Continued)

OTHER PUBLICATIONS

Abdel-Meguid Osman, "Reactions Between Chloro-p-benzoquinones and β-Naphtol", Journal of Organic Chemistry, 1957, vol. 22, Issue 3, pp. 342-344.*
(Continued)

*Primary Examiner* — Kyoung Lee
(74) *Attorney, Agent, or Firm* — Sughrue Mion, PLLC

(57) ABSTRACT

An organic thin film transistor having a semiconductor active layer containing a compound represented by the formula (1) has a high carrier mobility and a small change in the threshold voltage after repeated operation. $R^1$ to $R^{10}$ represent H or a substituent, provided that any two adjacent members among $R^1$ to $R^4$ and $R^6$ to $R^9$ are bonded to each other to form a substituted or unsubstituted benzene ring.

(Continued)

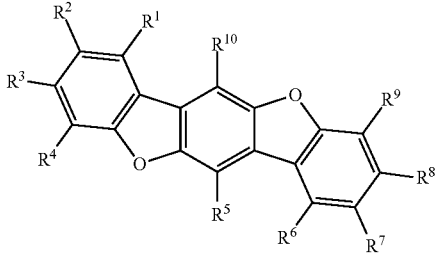

(51) Int. Cl.
*H01L 51/00* (2006.01)
*H01L 51/05* (2006.01)

(52) U.S. Cl.
CPC .......... *H01L 51/0558* (2013.01); *H01L 51/42* (2013.01); *Y02E 10/549* (2013.01)

(56) References Cited

U.S. PATENT DOCUMENTS

| 8,372,529 | B2 | 2/2013 | Kato et al. |
| 8,409,730 | B2 | 4/2013 | Kato et al. |
| 8,852,756 | B2 | 10/2014 | Vestweber et al. |
| 2008/0220285 | A1 | 9/2008 | Vestweber et al. |
| 2009/0261300 | A1 | 10/2009 | Watanabe et al. |
| 2009/0302743 | A1 | 12/2009 | Kato et al. |
| 2012/0074396 | A1 | 3/2012 | Meng et al. |
| 2012/0085995 | A1 | 4/2012 | Kato et al. |
| 2012/0112629 | A1 | 5/2012 | Kato et al. |
| 2013/0153874 | A1 | 6/2013 | Kato et al. |
| 2015/0031896 | A1 | 1/2015 | Vestweber et al. |

FOREIGN PATENT DOCUMENTS

| JP | 2010-45281 A | 2/2010 |
| WO | 2006/122630 A1 | 11/2006 |
| WO | 2009/148016 A1 | 12/2009 |
| WO | 2010/107244 A2 | 9/2010 |

OTHER PUBLICATIONS

Thorsten Vehoff et al., "Charge Transport in Organic Crystals: Role of Disorder and Topological Connectivity", J. Am. Chem. Soc., 2010, pp. 11702-11708, vol. 132, No. 33.
Kazuo Takimiya et al., "Thienoacene-Based Organic Semiconductors", Adv. Mater., 2011, pp. 4347-4370, vol. 23.
Molecular Electronics and Bioelectronics, The Japan Society of Applied Physics, 2011, pp. 9-12, vol. 22, No. 1.
Abdel-Meguid Osman, "Reactions Between Chloro-p-benzoquinones and β-Napthol", Journal of Organic Chemistry, Mar. 1, 1957, pp. 342-344, vol. 22, Issue 3.
International Search Report and Written Opinion dated Oct. 22, 2013 for PCT/JP2013/071323.
Office Action dated Jul. 14, 2015, issued by the Japan Patent Office in corresponding Japanese Application No. 2012-187059.
Office Action dated Feb. 18, 2016 from the Korean Intellectual Property Office issued in corresponding Korean Application No. 10-2015-7007398.
English excerpt of Molecular Electronics and Bioelectronics, The Japan Society of Applied Physics, 2011, pp. 9-12, vol. 22, No. 1.
International Preliminary Report on Patentability (IPRP) of Chapter I, i.e., International Search Opinion dated Mar. 12, 2015, issued by the International Bureau of WIPO in counterpart International Application No. PCT/JP2013/071323.
Office Action dated Oct. 6, 2016, from the Intellectual Property Office of Taiwan in counterpart Taiwanese Application No. 102129073.

\* cited by examiner

15 Claims, 2 Drawing Sheets

ORGANIC THIN FILM TRANSISTOR, ORGANIC SEMICONDUCTOR THIN FILM, AND ORGANIC SEMICONDUCTOR MATERIAL

CROSS-REFERENCE TO RELATED APPLICATIONS

This application is a Continuation of PCT International Application No. PCT/JP2013/071323, filed Aug. 7, 2013, which claims priority under 35 U.S.C. Section 119(a) to Japanese Patent Application No. 2012-187059 filed on Aug. 27, 2012. Each of the above applications is hereby expressly incorporated by reference, in its entirety, into the present application.

BACKGROUND OF THE INVENTION

Field of the Invention

The present invention relates to an organic thin film transistor, an organic semiconductor thin film, and an organic semiconductor material. Specifically, the invention relates to an organic semiconductor material for a non-light-emitting organic semiconductor device containing a compound having a benzobisbenzofuran derivative structure (which may be hereinafter referred to as a BBBF derivative structure), an organic semiconductor thin film containing the material, and an organic thin film transistor using the thin film.

Background Art

A device using an organic semiconductor material is expected to have various advantages as compared to a device using an ordinary inorganic semiconductor material, such as silicon, and thus is receiving a high level of interest. Examples of the device using an organic semiconductor material include a photoelectric conversion device using an organic semiconductor material as a photoelectric conversion material, such as an organic thin film solar cell and a solid-state imaging device, and a non-light-emitting organic transistor. A device using an organic semiconductor material has a possibility of producing a large area device at a low temperature and low cost, as compared to a device using an inorganic semiconductor material. Furthermore, the material characteristics may be easily changed by changing the molecular structure thereof, thereby providing a wide range of varieties of the materials, and thus functions and devices that are not achieved with an inorganic semiconductor material may be realized.

For example, Patent Reference 1 describes the compound represented by the following general formula having as a partial structure a condensed ring containing five rings including aromatic heterocyclic rings (in which ring A and ring B each represent a benzene ring or a particular 5-membered aromatic heterocyclic ring; $T^1$ and $T^2$ each represent sulfur, selenium, tellurium, oxygen, phosphorus, boron or aluminum; $R^1$ to $R^4$ each represent a hydrogen atom, an alkyl group, or the like; and l and m each represent 0 or 1). Patent Reference 1 describes that the compound represented by the following general formula may form a semiconductor active layer and may be an organic semiconductor material that is capable of forming the film by coating. In the literature, the compound is used as an organic semiconductor material and forms an organic thin film, but the transistor characteristics and the like thereof are not described.

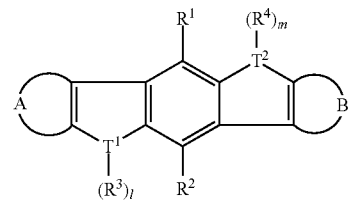

Patent Reference 2 and Non-patent Reference 1 describe the use of a polycyclic condensed ring compound containing an aromatic heterocyclic ring in an organic transistor. Patent Reference 2 suggests the application of an organic compound having a benzobisbenzofuran (which may be hereinafter referred to as BBBF) skeleton to an organic thin film transistor, but does not describe an example that show the purpose as an organic transistor and the transistor characteristics. Non-patent Reference 1 suggests that some of compounds having a BBBF skeleton appear promising as a material for an organic electroluminescent transistor. However, the organic electroluminescent transistor only has transistor characteristics that are in an elementary level and fails to achieve a practical level due to the low mobility.

Patent Reference 3 describes an organic compound having a benzobisnaphthofuran (which may be hereinafter referred to as BBNF) skeleton, in addition to an organic compound having a BBBF skeleton, and describes that the organic compound is useful as a material for an organic EL device. Patent Reference 3 only describes the usefulness as a material for an organic EL device, but does not describe or suggest the application thereof to an organic thin film transistor.

CITATION LIST

Patent References

Patent Reference 1: JP-A-2008-81494
Patent Reference 2: WO 2006/122630
Patent Reference 3: JP-A-2010-45281

Non-Patent Reference

Non-patent Reference 1: Molecular Electronics and Bioelectronics, The Japan Society of Applied Physics, vol. 22, pp. 9-12 (2011)

SUMMARY OF INVENTION

As described in Patent Reference 3, the usefulness as an organic EL device material of a polycyclic condensed ring compound containing an aromatic heterocyclic ring, such as a BBBF skeleton and BBNF skeleton, has been known. However, it may not be said that a compound that is useful as an organic EL device material is immediately useful as a semiconductor material for an organic thin film transistor. This is because the characteristics demanded for the organic compound are different between an organic EL device and an organic thin film transistor. Specifically, an organic thin film transistor requires carrier transport in a long distance (generally from several micrometers to several hundred micrometers) between electrodes in the thin film in-plane direction, which is different from the case of an organic EL device and the like, which require charge transport in a distance (generally from several nanometers to several hundred nanometers) in the thin film thickness direction, and thus demands a remarkably high carrier mobility. Accordingly, an organic compound that has high crystallinity is demanded as the semiconductor material for an organic thin film transistor. On the other hand, a device that has a high light emission efficiency and achieves uniform in-plane light emission is demanded as the organic EL device. In general, an organic compound having high crystallinity may cause light emission defects, such as in-plane unevenness in electric field intensity, in-plane unevenness in light emission, and light emission quenching, and therefore the organic EL device material may not be enhanced in crystallinity. Accordingly, even when an organic compound that constitutes an organic EL device is diverted as it is to an organic semiconductor material, good transistor characteristics may not be obtained.

As a result of practical application by the present inventors of the polycyclic condensed ring compounds containing an aromatic heterocyclic ring, such as a BBBF skeleton, that are applied to an organic EL device in the aforementioned Patent References to an organic thin film transistor, a problem has been found that sufficient transistor characteristics are not obtained. Specifically, it has been found as a result of investigations made by the inventors that in the case where the compounds, the structures of which are specifically described in the Patent References, are applied as an organic semiconductor material to an organic thin film transistor, a high carrier mobility is not obtained. Furthermore, it has been found as a result of investigations made by the inventors that in the case where the compounds are applied as an organic semiconductor material to an organic thin film transistor, which is then operated repeatedly, the change in the threshold voltage is increased. The increase of the threshold voltage brings about such problems as deterioration in reliability of the transistor, and failure of long-term use of the semiconductor.

Under the circumstances, the inventors have made investigations for providing an organic thin film transistor showing good transistor characteristics for solving the aforementioned problems. Specifically, an object to be achieved by the inventors is to provide a semiconductor material that has a high carrier mobility and a small change in the threshold voltage after repeated operation, and to provide an organic thin film transistor that has good transistor characteristics by applying the semiconductor material thereto.

As a result of earnest investigations made by the inventors for solving the problem, it has been found that a BBNF derivative having a particular structure has high crystallinity and provides an organic thin film advantageous to carrier transport. Accordingly, the inventors have succeeded to provide an organic thin film transistor that has a high carrier mobility, and thus the invention has been completed.

The inventors have also found that the organic thin film transistor obtained in the invention has a small change in the mobility before and after heating the device and a small change in the threshold voltage after repeated operation, and have succeeded to provide an organic thin film transistor that is capable of being used stably for a prolonged period of time.

Specifically, the invention includes the following aspects.

(1) An organic thin film transistor having a semiconductor active layer containing a compound represented by the following general formula (1):

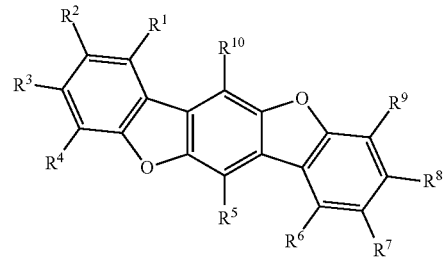

General Formula (1)

wherein in the general formula (1), $R^1$ to $R^{10}$ each independently represent a hydrogen atom or a substituent, provided that any two adjacent members among $R^1$ to $R^4$ and $R^6$ to $R^9$ are bonded to each other to form a substituted or unsubstituted benzene ring, i.e. provided that at least one pair of $R^1$ and $R^2$, $R^2$ and $R^3$, $R^3$ and $R^4$, $R^6$ and $R^7$, $R^7$ and $R^8$, and $R^8$ and $R^9$ forms a substituted or unsubstituted benzene ring with the two $R^n$ constituting the pair being bonded to each other in which n is an integer of 1 to 4 and 6 to 9.

(2) The organic thin film transistor according to the item (1), wherein the compound represented by the general formula (1) is represented by the following general formula (2):

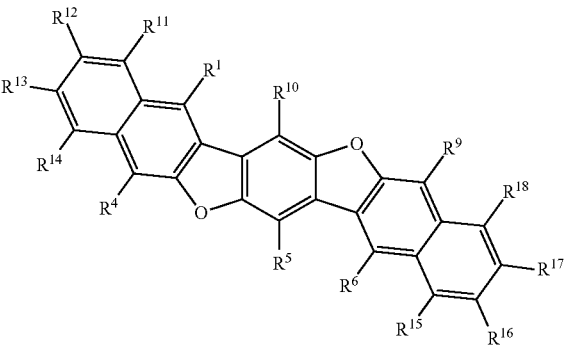

General Formula (2)

wherein in the general formula (2), $R^1$, $R^4$ to $R^6$ and $R^9$ to $R^{18}$ each independently represent a hydrogen atom or a substituent.

(3) The organic thin film transistor according to the item (2), wherein at least one of $R^1$, $R^4$ to $R^6$ and $R^9$ to $R^{18}$ represents a substituent represented by the following general formula (W):

*-L-R            General Formula (W)

wherein in the general formula (W), a position shown by * represents a bonding position to the benzobisnaphthofuran skeleton; L represents a single bond or a divalent linking group; and R represents an alkyl group having 2 or more carbon atoms, an oligoethyleneoxy group having a number of repetition of ethyleneoxy units of 2 or more, or an oligosiloxane group having 2 or more silicon atoms.

(4) The organic thin film transistor according to the item (2), wherein the compound represented by the general formula (2) is represented by the following general formula (3-1) or (3-2)

General Formula (3-1)

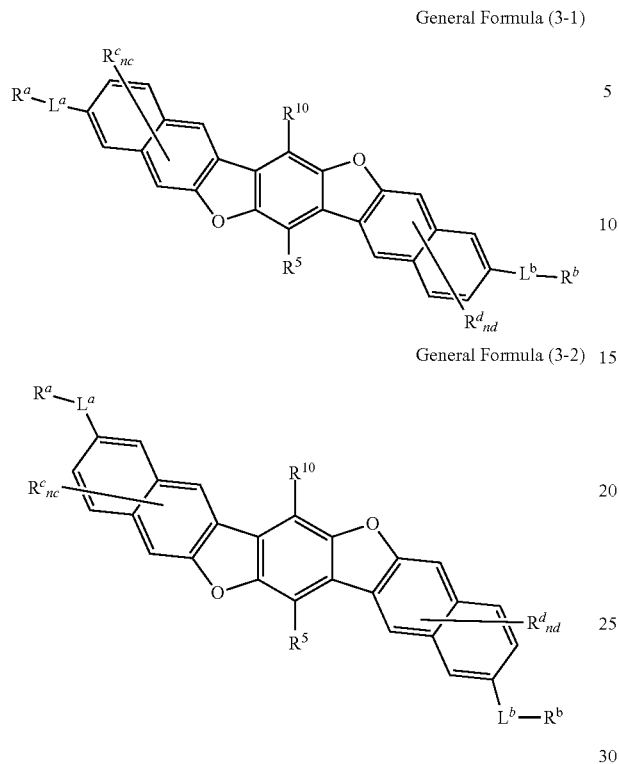

General Formula (3-2)

wherein in the general formulae (3-1) and (3-2), $R^5$ and $R^{10}$ each independently represent a hydrogen atom or a substituent; $L^a$ and $L^b$ each independently represent a single bond or a divalent linking group; $R^a$ and $R^b$ each independently represent an alkyl group having 2 or more carbon atoms, an oligoethyleneoxy group having a number of repetition of ethyleneoxy units of 2 or more, or an oligosiloxane group having 2 or more silicon atoms; $R^c$ and $R^d$ each independently represent a substituent; and nc and nd each independently represent an integer of from 0 to 5.

(5) The organic thin film transistor according to the item (4), wherein in the general formula (3-1) or the general formula (3-2), $L^a$ and $L^b$ each are selected from a single bond and the following general formulae (L-1) to (L-12):

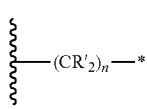
(L-1)

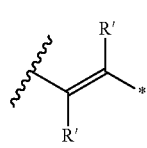
(L-2)

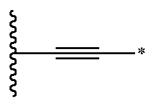
(L-3)

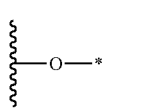
(L-4)

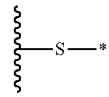
(L-5)

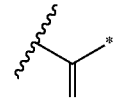
(L-6)

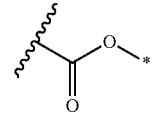
(L-7)

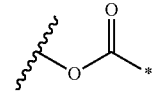
(L-8)

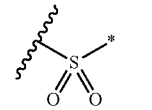
(L-9)

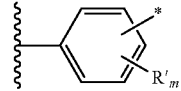
(L-10)

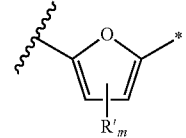
(L-11)

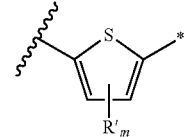
(L-12)

wherein in the general formulae (L-1) to (L-12), a position shown by a wave line represents a bonding position to the benzobisnaphthofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11) and (L-12) each independently represent a hydrogen atom or a substituent.

(6) The organic thin film transistor according to the item (4), wherein in the general formula (3-1) or the general formula (3-2), both $L^a$ and $L^b$ each are a single bond.

(7) The organic thin film transistor according to any one of the items (4) to (6), wherein in the general formula (3-1) or the general formula (3-2), all $R^a$, $R^b$, $R^c$ and $R^d$ each are an alkyl group.

(8) The organic thin film transistor according to any one of the items (4) to (6), wherein in the general formula (3-1) or the general formula (3-2), all $R^a$, $R^b$, $R^c$ and $R^d$ each are an alkyl group having from 6 to 12 carbon atoms.

(9) The organic thin film transistor according to the item (1), wherein the compound represented by the general formula (1) is represented by the following general formula (4):

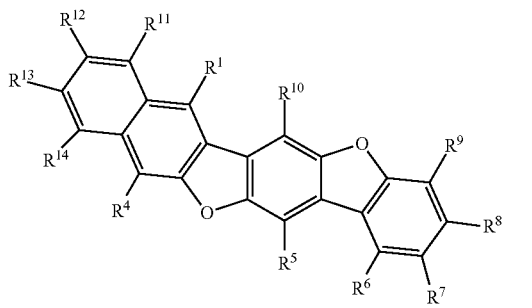

General Formula (4)

wherein in the general formula (4), $R^1$ and $R^4$ to $R^{14}$ each independently represent a hydrogen atom or a substituent.

(10) The organic thin film transistor according to the item (9), wherein in the general formula (4), at least one of $R^1$ and $R^4$ to $R^{14}$ represents a substituent represented by the following general formula (W):

*-L-R   General Formula (W)

wherein in the general formula (W), a position shown by * represents a bonding position to the benzobisbenzofuran skeleton; L represents a single bond or a divalent linking group; and R represents an alkyl group having 2 or more carbon atoms, an oligoethyleneoxy group having a number of repetition of ethyleneoxy units of 2 or more, or an oligosiloxane group having 2 or more silicon atoms.

(11) A compound represented by the following general formula (1'):

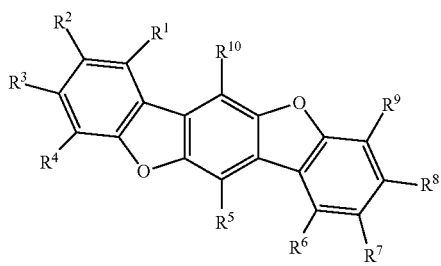

General Formula (1')

wherein in the general formula (1'), $R^1$ to $R^{10}$ each independently represent a hydrogen atom or a substituent, provided that any two adjacent members among $R^1$ to $R^4$ and $R^6$ to $R^9$ are bonded to each other to form a substituted or unsubstituted benzene ring, and in the case where $R^2$ and $R^3$ are bonded to each other to form a benzene ring, and $R^7$ and $R^8$ are bonded to each other to form a benzene ring, at least one of the benzene rings has a substituent.

(12) The compound according to the item (11), wherein the compound represented by the general formula (1') is represented by the following general formula (2'):

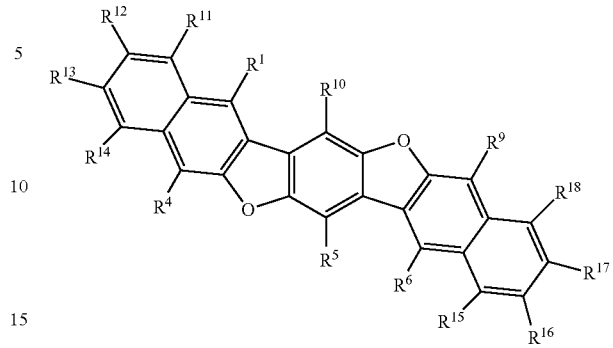

General Formula (2')

wherein in the general formula (2'), $R^1$, $R^4$ to $R^6$ and $R^9$ to $R^{18}$ each independently represent a hydrogen atom or a substituent, provided that at least one of $R^1$, $R^4$ to $R^6$ and $R^9$ to $R^{18}$ represents a substituent.

(13) The compound according to the item (12), wherein the compound represented by the general formula (2') is represented by the following general formula (3-1') or (3-2'):

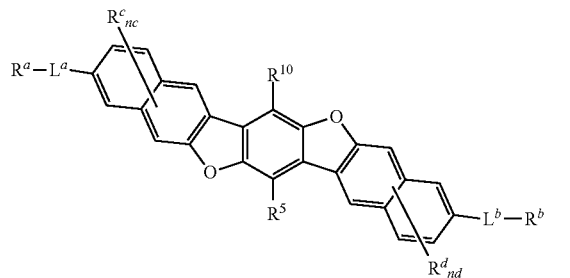

General Formula (3-1')

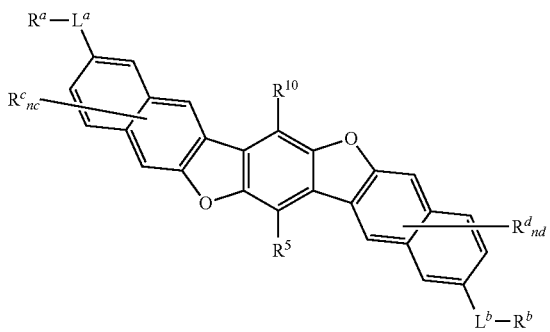

General Formula (3-2')

wherein in the general formulae (3-1') and (3-2'), $R^5$ and $R^{10}$ each independently represent a hydrogen atom or a substituent; $L^a$ and $L^b$ each independently represent a single bond or a divalent linking group; $R^a$ and $R^b$ each independently represent an alkyl group having 2 or more carbon atoms, an oligoethyleneoxy group having a number of repetition of 2 or more, or an oligosiloxane group having a number of repetition of 2 or more; $R^c$ and $R^d$ each independently represent a substituent; and nc and nd each independently represent an integer of from 0 to 5.

(14) An organic semiconductor material for a non-light-emitting organic semiconductor device, containing a compound represented by the general formula (1) according to the item (1).

(15) A material for an organic thin film transistor, containing a compound represented by the general formula (1) according to the item (1).

(16) A coating solution for a non-light-emitting organic semiconductor device, containing a compound represented by the general formula (1) according to the item (1).

(17) A coating solution for a non-light-emitting organic semiconductor device, containing a compound represented by the general formula (1) according to the item (1) and a polymer binder.

(18) An organic semiconductor thin film containing the coating solution according to the item (16) having been coated and dried.

(19) An organic semiconductor thin film containing the coating solution according to the item (17) having been coated and dried.

According to the invention, a semiconductor material that has high crystallinity and forms an organic thin film advantageous for carrier transport may be provided, and thereby an organic thin film transistor that has a high carrier mobility may be provided.

According to the invention, furthermore, an organic thin film transistor that also has a small change in the threshold voltage after repeated operation may be provided, and thereby the organic thin film of the organic thin film transistor may have high chemical stability, a high film density, and the like, and may be capable of effectively functioning as a transistor for a prolonged period of time.

DESCRIPTION OF EMBODIMENTS

Figure 1:
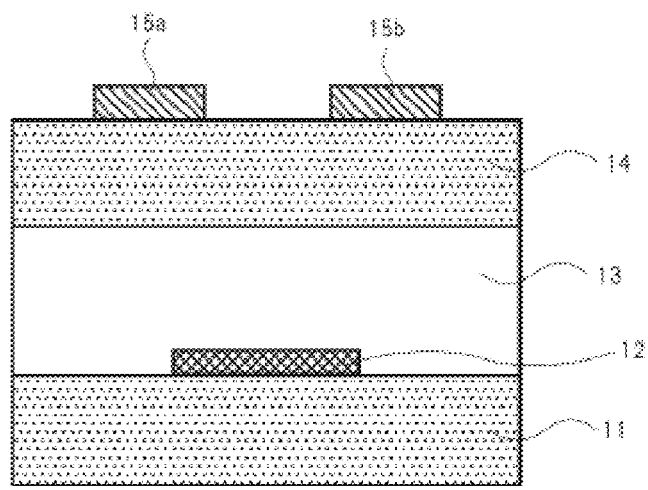
FIG. 1 is a cross sectional view schematically showing a structure of an organic thin film transistor device according to the invention.

The invention will be described in detail below. The following description of constitutional elements may be made based on representative embodiments and specific examples, but the invention is not limited to the embodiments and examples. In this specification, numeric ranges expressed using "to" means a numeric range involving the numerals recited before and after "to" as the lower limit and the upper limit.

In the invention, the hydrogen atoms that are referred for the description of the general formulae herein include isotopes thereof (such as a deuterium atom) unless otherwise indicated. The atoms constituting the substituents also include isotopes thereof.

Organic Thin Film Transistor

The organic thin film transistor of the invention has a semiconductor active layer, and the semiconductor active layer contains a compound represented by the following general formula (1). Examples of the basic laminated structure thereof include a structure that contains a substrate as the lowermost layer having disposed thereon in this order an electrode, an insulator layer, a semiconductor active layer (i.e., an organic semiconductor layer), and two electrodes (i.e., a bottom gate-top contact structure). In this structure, the electrode on the upper surface of the substrate as the lowermost layer is provided on a part of the substrate, and the insulator layer is disposed in such a manner that the insulator layer is in contact with the substrate in the area except for the electrode. The two electrodes provided on the upper surface of the semiconductor active layer are disposed in such a manner that the electrodes are separated from each other.

Benzobisbenzofuran Derivative

One of the features of the invention is that the semiconductor active layer contains a compound represented by the following general formula (1)

General Formula (1)

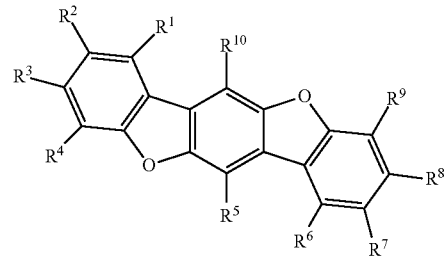

In the general formula (1), $R^1$ to $R^{10}$ each independently represent a hydrogen atom or a substituent, provided that any two adjacent members among $R^1$ to $R^4$ and $R^6$ to $R^9$ are bonded to each other to form a substituted or unsubstituted benzene ring.

The substituted or unsubstituted benzene ring is formed by bonding any two adjacent members among $R^1$ to $R^4$ and $R^6$ to $R^9$ to each other in the general formula (1), and more specifically, the substituted or unsubstituted benzene ring is formed by at least one case selected from the case where $R^1$ and $R^2$ are bonded to each other, the case where $R^2$ and $R^3$ are bonded to each other, the case where $R^3$ and $R^4$ are bonded to each other, the case where $R^6$ and $R^7$ are bonded to each other, the case where $R^7$ and $R^8$ are bonded to each other, and the case where $R^8$ and $R^9$ are bonded to each other.

It is preferred in this case that any adjacent two of $R^1$ to $R^4$ are bonded to each other to form at least one benzene ring, and any adjacent two of $R^6$ to $R^9$ are bonded to each other to form a benzene ring. Specifically, preferred examples thereof include: an embodiment, in which $R^1$ and $R^2$ are bonded to each other, and $R^6$ and $R^7$ are bonded to each other, so as to form a substituted or unsubstituted benzene ring respectively; an embodiment, in which $R^2$ and $R^3$ are bonded to each other, and $R^7$ and $R^8$ are bonded to each other, so as to form a substituted or unsubstituted benzene ring respectively; and an embodiment, in which $R^3$ and $R^4$ are bonded to each other, and $R^7$ and $R^8$ are bonded to each other, so as to form a substituted or unsubstituted benzene ring respectively. The substituted or unsubstituted benzene rings formed at these positions appropriately enhance the π-conjugated system, which is advantageous for the HOMO level, the rearrangement energy of cation, the crystalline structure, and the like, and thereby an organic thin film that is enhanced in the carrier transport characteristics may be provided.

The benzene ring preferably has a substituent as described later. In the case where $R^2$ and $R^3$ are bonded to each other to form a benzene ring, and $R^7$ and $R^8$ are bonded to each other to form a benzene ring, in particular, at least one of the benzene rings preferably has a substituent. The substituent on the benzene ring may enhance the solubility to a solvent in a solvent and also may enhance the alignment order of the molecules in the thin film. According thereto, the compound may enhance the production efficiency of the organic thin film capable of being applied to an organic thin film transistor, and may reduce the production cost. The compound may also enhance the carrier transport characteristics, such as the carrier mobility, and the chemical and physical stability of the thin film.

Examples of the substituent capable of being $R^1$ to $R^{10}$ and the substituent capable of being substituted on the benzene ring that is formed by bonding adjacent two of $R^1$ to $R^4$ and $R^6$ to $R^9$ to each other include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group, a cyano group, a hydroxyl group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imido group, a phosphino group, a phosphinyl group, a phosphinyloxy group, a phosphinylamino group, a phosphono group, a silyl group, a hydrazino group, a ureido group, a boric acid group (—B(OH)$_2$), a phosphato group (—OPO(OH)$_2$), a sulfato group (—OSO$_3$H), and other known substituents.

In the invention, the compound represented by the general formula (1) is preferably a compound represented by the following general formula (2):

General Formula (2)

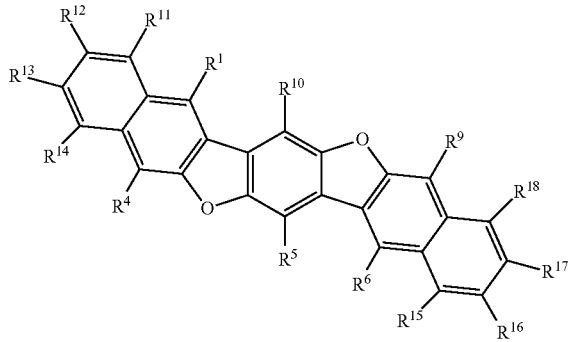

In the general formula (2), $R^1$, $R^4$ to $R^6$ and $R^9$ to $R^{18}$ each independently represent a hydrogen atom or a substituent.

In the invention, in the general formula (2), at least one of $R^1$, $R^4$ to $R^6$ and $R^9$ to $R^{18}$ preferably represents a substituent, and at least one thereof preferably represents a substituent represented by the following general formula (W):

\*-L-R     General Formula (W)

In the general formula (W), a position shown by * represents a bonding position to the benzobisnaphthofuran skeleton; L represents a single bond or a divalent linking group; and R represents an alkyl group having 2 or more carbon atoms, an oligoethyleneoxy group having a number of repetition of ethyleneoxy units of 2 or more, or an oligosiloxane group having 2 or more silicon atoms.

In the case where R represents an alkyl group, the number of carbon atoms thereof is preferably from 2 to 18, more preferably from 6 to 12, and further preferably from 6 to 10. The alkyl group capable of being R may be any of linear, branched and cyclic, and a substituted or unsubstituted alkyl group may be used therefor.

In the case where R represents an oligoethyleneoxy group, the number of repetition of ethyleneoxy units is preferably from 2 to 4, and more preferably from 2 to 3. The end hydroxyl group of the oligoethyleneoxy group is preferably sealed. In this case, the hydroxyl group is preferably sealed with an alkyl group having from 1 to 3 carbon atoms. The hydroxyl group is preferably sealed, for example, with a methyl group or an ethyl group.

In the case where R represents an oligosiloxane group, the number of repetition of siloxane units is preferably from 2 to 4, and more preferably from 2 to 3. The Si atom is preferably bonded to a hydrogen atom or an alkyl group. In the case where the Si atom is bonded to an alkyl group, the number of carbon atoms of the alkyl group is preferably from 1 to 3, and for example, the Si atom is preferably bonded to a methyl group or an ethyl group. The Si atom may be bonded to the same alkyl groups or may be bonded to different alkyl groups or a hydrogen atom. All the siloxane units constituting the oligosiloxane group may be the same as each other or may be different from each other, and preferably are the same as each other.

L represents a single bond or a divalent linking group. The divalent linking group may have polarity or may not have polarity. The divalent linking group may contain an unsaturated bond or may not contain an unsaturated bond. The number of atoms constituting the divalent linking group is preferably from 1 to 10, more preferably from 1 to 6, and further preferably from 1 to 3. Preferred examples of the divalent linking group include groups represented by the following general formulae (L-1) to (L-12):

(L-1)

(L-2)

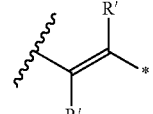
(L-3)

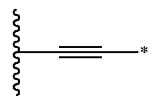
(L-4)

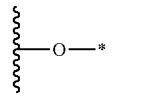
(L-5)

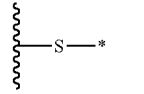

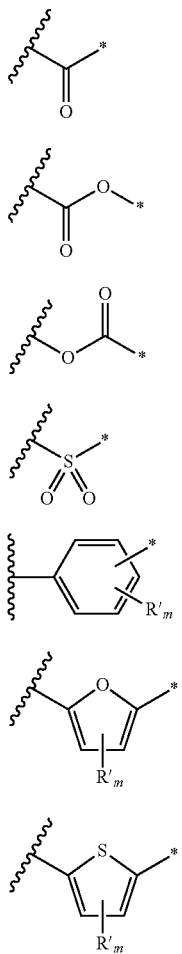

(L-6)
(L-7)
(L-8)
(L-9)
(L-10)
(L-11)
(L-12)

In the general formulae (L-1) to (L-12), a position shown by a wave line represents a bonding position to the BBNF skeleton; a position shown by * represents the bonding position to R in the general formula (W), provided that in the general formulae (L-10) to (L-12), a group represented by one of the general formulae (L-10) to (L-12) may be inserted between the position shown by * and R. n in the general formula (L-1) represents an integer of 1 or more, preferably an integer of from 1 to 10, more preferably an integer of from 1 to 6, and further preferably an integer of from 1 to 3.

Examples of the substituent represented by R' in the general formulae (L-1), (L-2), (L-10), (L-11) and (L-12) include ones exemplified for the substituent capable of being $R^1$ to $R^{10}$ in the general formula (1). m in the general formula (L-10) represents 4, and m in the general formulae (L-11) and (L-12) represents 2.

L preferably represents one of a single bond and divalent linking groups represented by the general formulae (L-1), (L-3), (L-4), (L-6), (L-10), (L-11) and (L-12), more preferably one of a single bond and divalent linking groups represented by the general formulae (L-1), (L-3), (L-4), (L-10) and (L-12), particularly preferably one of a single bond and divalent linking groups represented by the general formulae (L-4), (L-10) and (L-12), and most preferably a single bond.

In the general formula (2), $R^1$, $R^4$ to $R^6$ and $R^9$ to $R^{18}$ may each represent a substituent that has a structure other than the general formula (W). Specific examples of the substituent include the specific examples for the substituent R' in the general formulae (L-1), (L-2), (L-10), (L-11) and (L-12).

Most of the ordinary compounds having a BBBF-like structure have been compounds containing a chalcogen (e.g., S and Se), but it has been difficult to provide an organic thin film having good film quality and a molecular packing advantageous for carrier transport, from the chalcogen (e.g., S and Se)-containing compound.

Under the circumstances, the invention uses as an organic semiconductor material the compound that has a particular BBBF skeleton containing oxygen atoms and the substituents having the particular structure, as represented by the general formula (1). It is considered that the organic semiconductor material forms a herringbone structure suitable for carrier transport in the organic thin film facilitating the formation of a two-dimensional overlap of orbitals (the advantage of the herringbone structure for carrier transport is described, for example, in Adv. Mater., vol. 23, pp. 4347-4370 (2011)). Accordingly, it is considered that the compound of the invention achieves good film quality and a high carrier mobility and may be favorably used in an organic thin film transistor.

In the invention, in the general formula (2), one of $R^{12}$, $R^{13}$, $R^{16}$ and $R^{17}$ preferably represents a substituent represented by the general formula (W), and two positions of $R^{12}$ or $R^{13}$ and $R^{16}$ or $R^{17}$ are preferably substituted.

It is considered that the reason why the substitution positions in the general formula (2) are preferably the aforementioned positions is that such a compound has a good chemical stability and that these positions are advantageous also from the standpoint of the HOMO level and the molecular packing in the film. In the case where the substituents are substituted at two positions of $R^{12}$ or $R^{13}$ and $R^{16}$ or $R^{17}$, in particular, a high carrier concentration may be obtained.

The compound represented by the general formula (2) is preferably represented by the following general formula (3-1) or (3-2):

General Formula (3-1)

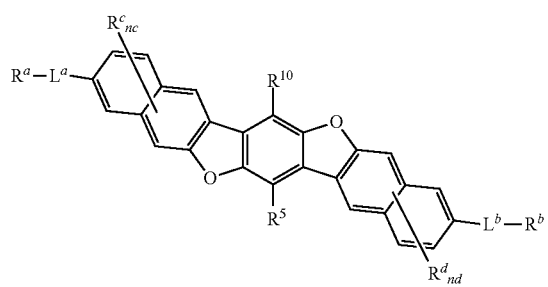

General Formula (3-2)

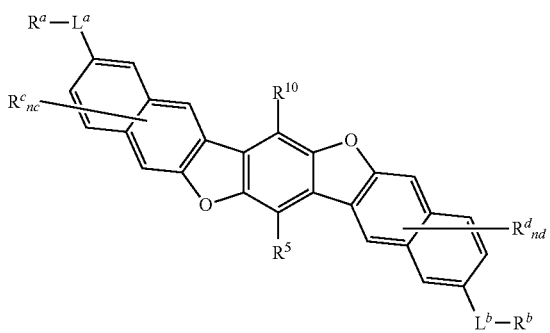

In the general formulae (3-1) and (3-2), $R^5$ and $R^{10}$ each independently represent a hydrogen atom or a substituent; $L^a$ and $L^b$ each independently represent a single bond or a divalent linking group; $R^a$ and $R^b$ each independently represent an alkyl group having 2 or more carbon atoms, an oligoethyleneoxy group having a number of repetition of ethyleneoxy units of 2 or more, or an oligosiloxane group having 2 or more silicon atoms; $R^c$ and $R^d$ each independently represent a substituent; and nc and nd each independently represent an integer of from 0 to 5.

In the invention, in the general formulae (3-1) and (3-2), all $R^a$, $R^b$, $R^c$ and $R^d$ each are preferably an alkyl group. When all $R^a$, $R^b$, $R^c$ and $R^d$ each are an alkyl group, the chemical stability may be enhanced. Examples of the alkyl group used include a linear, branched or cyclic unsubstituted or substituted alkyl group.

In the invention, in the general formulae (3-1) and (3-2), all $R^a$, $R^b$, $R^c$ and $R^d$ each are more preferably an alkyl group having from 6 to 12 carbon atoms from the standpoint of the chemical stability and the carrier transport property.

All $R^a$, $R^b$, $R^a$ and $R^d$ each are also preferably a linear alkyl group having 10 or less carbon atoms. The number of carbon atoms is preferably 10 or less, more preferably 8 or less, and further preferably 7 or less, and thereby the resulting compound may be enhanced in the solubility in a solvent. According thereto, the compound may enhance the production efficiency of the organic thin film capable of being applied to an organic thin film transistor, and may reduce the production cost.

In the invention, in the general formulae (3-1) and (3-2), both $L^a$ and $L^b$ each are preferably a single bond from the standpoint of the chemical stability and the carrier transport property.

In the compounds represented by the general formula (1), a compound represented by the general formula (1') is a novel compound. In the compounds represented by the general formula (2), a compound represented by the general formula (2') is a novel compound.

Specific examples of the compound represented by the general formula (1) are shown below, but the compound represented by the general formula (1) capable of being used in the invention is not construed as being limited to the specific examples.

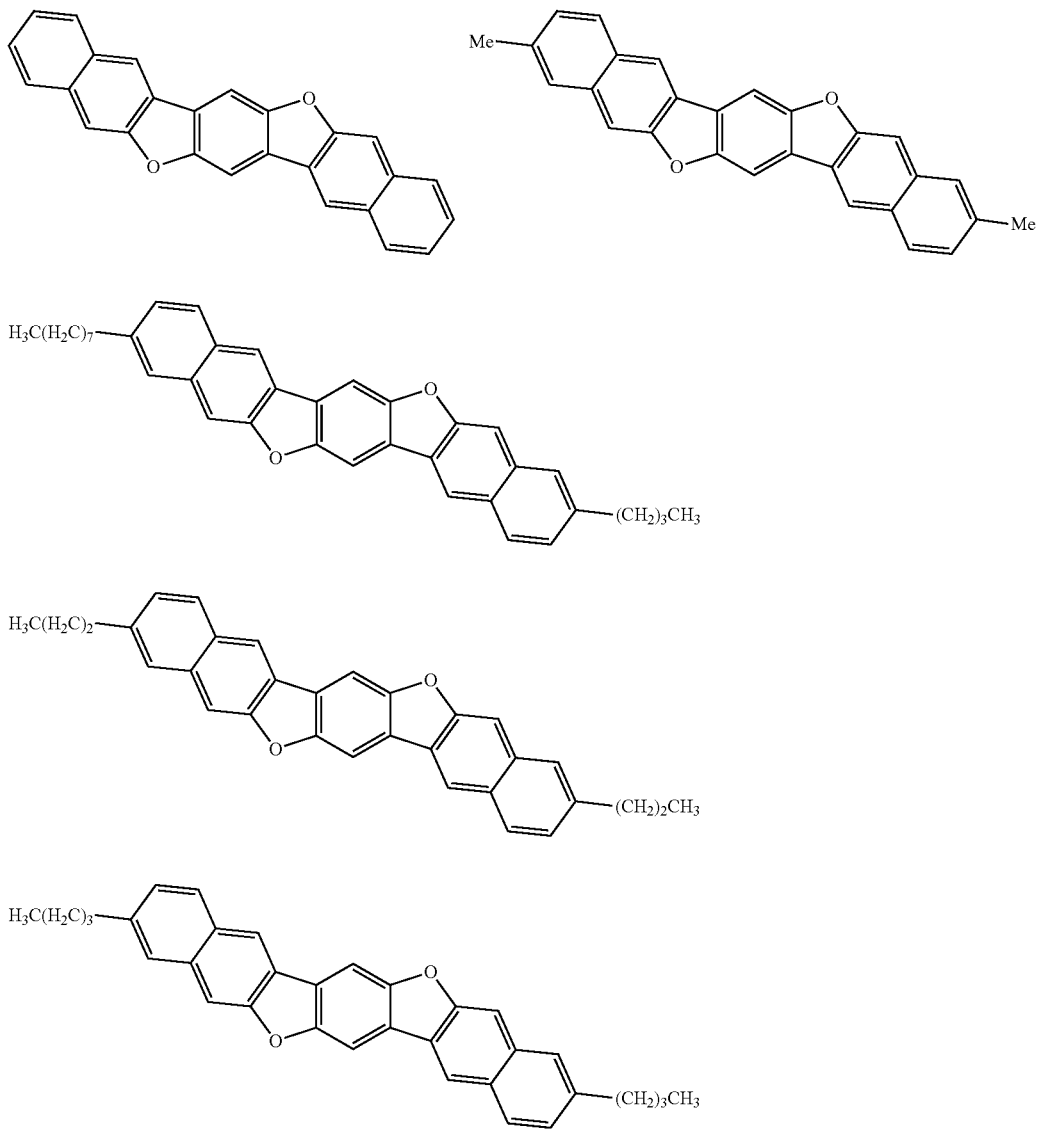

-continued
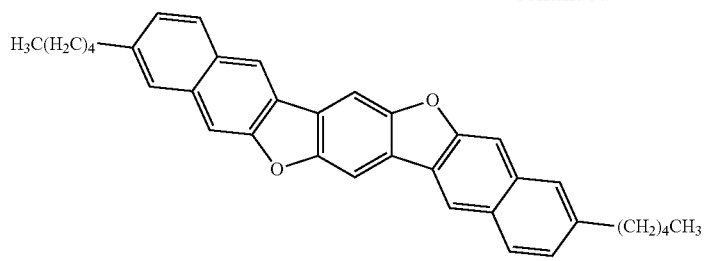
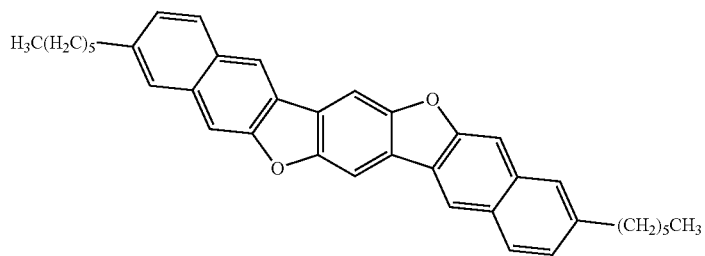
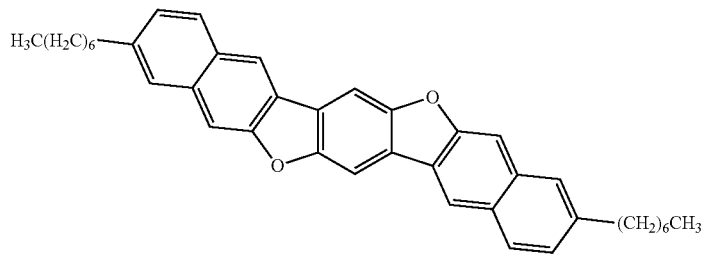
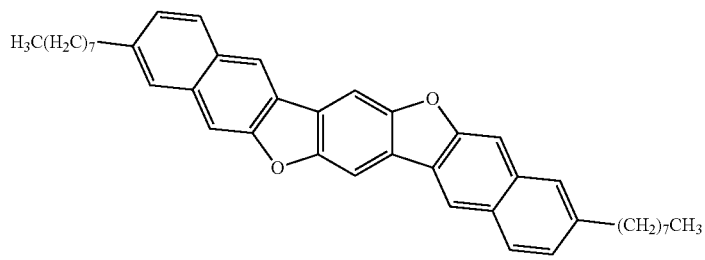
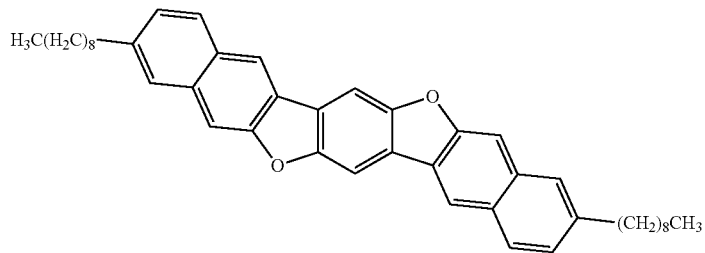
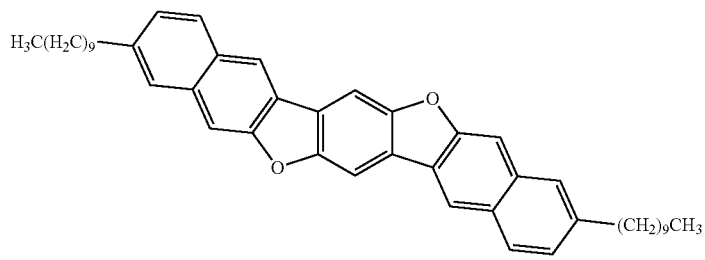

-continued
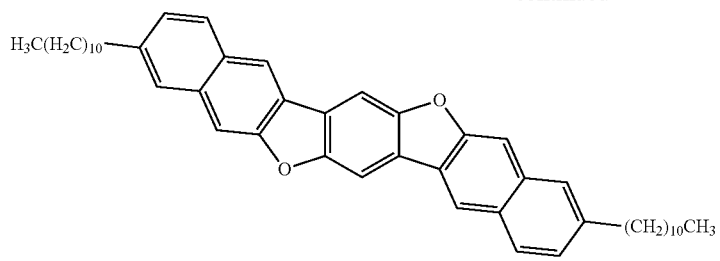
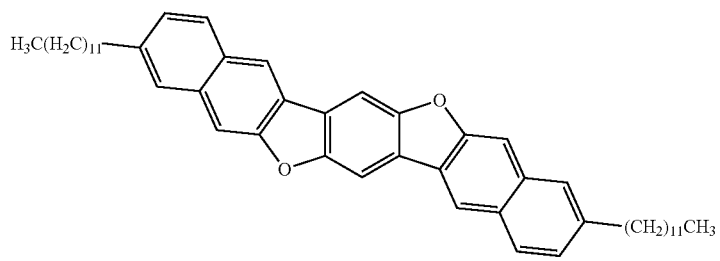
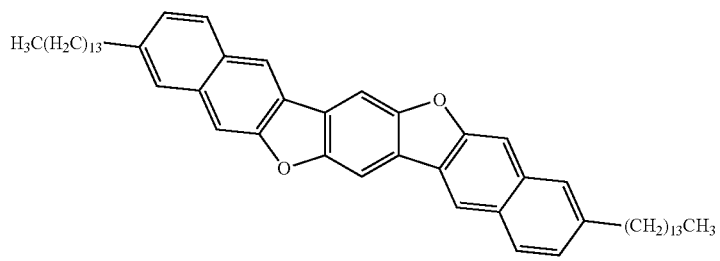
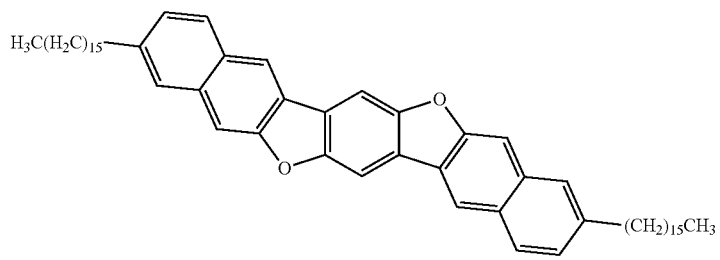
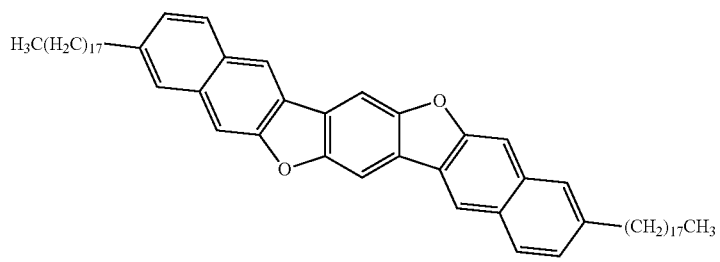
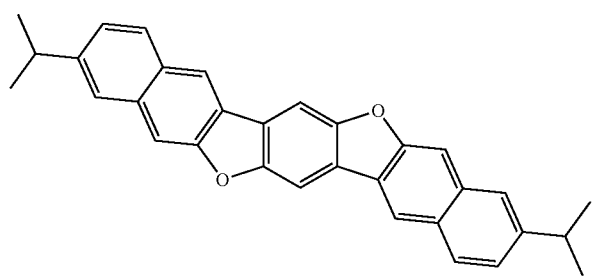

-continued
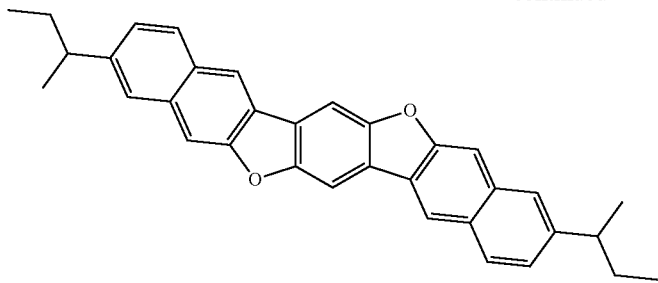
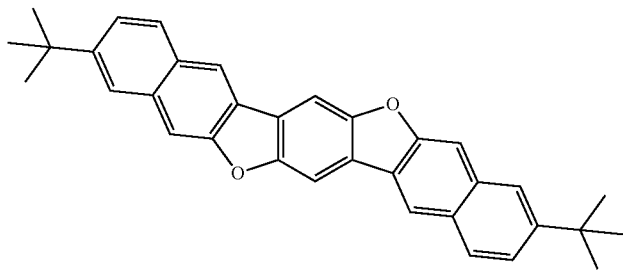
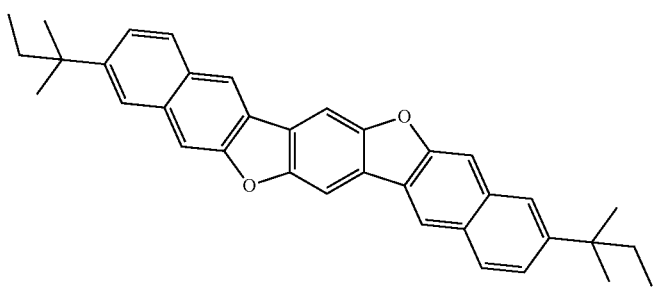
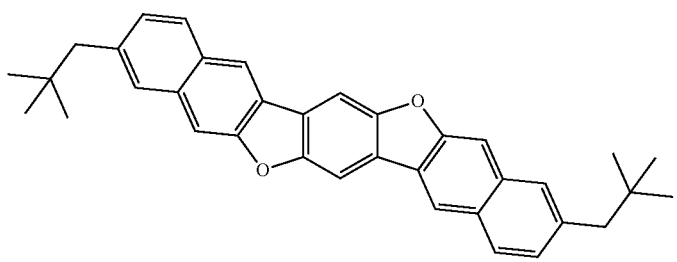
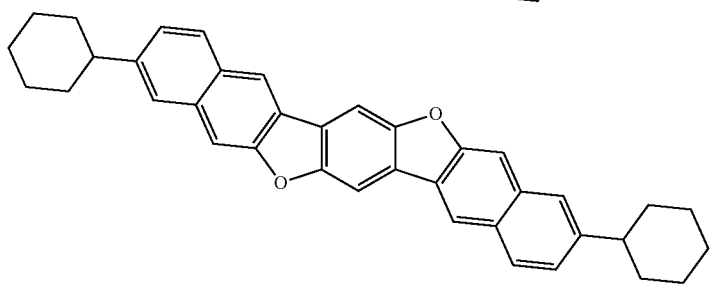
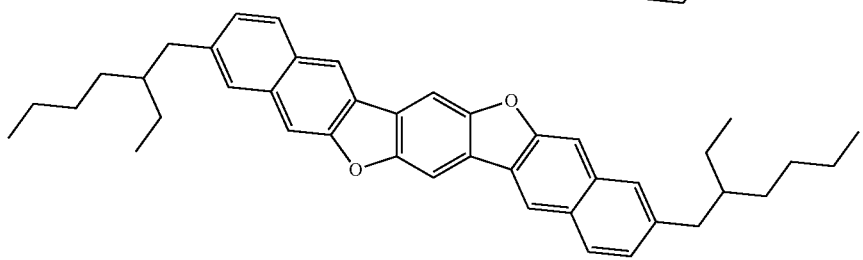

-continued
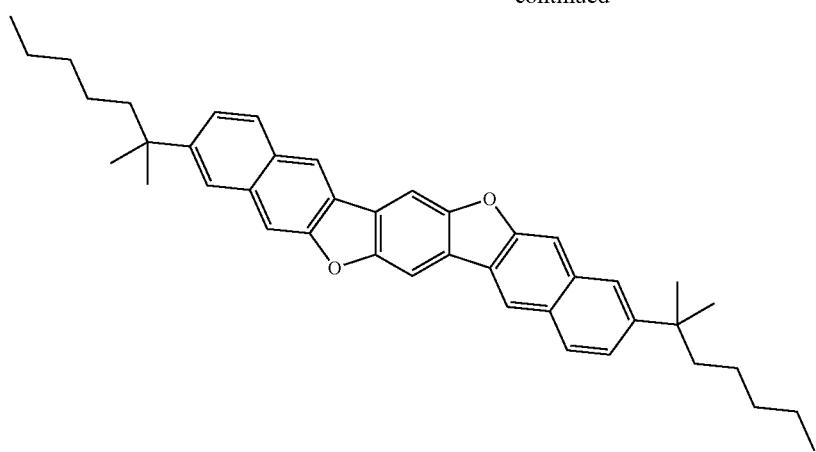
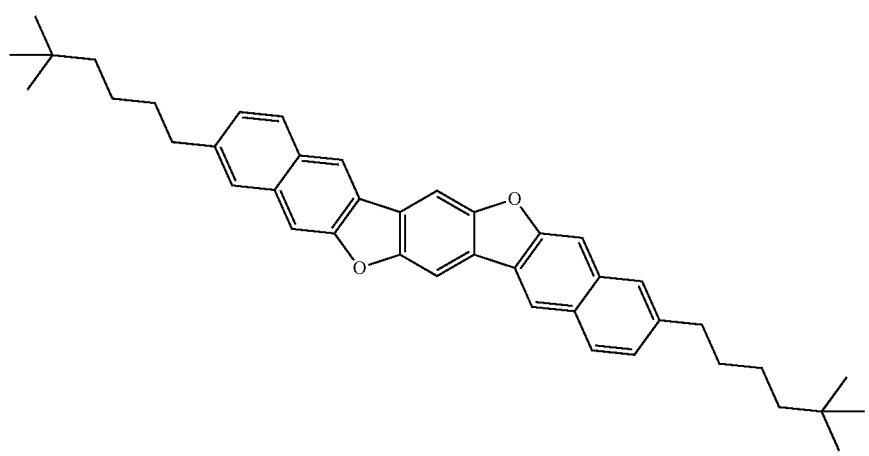
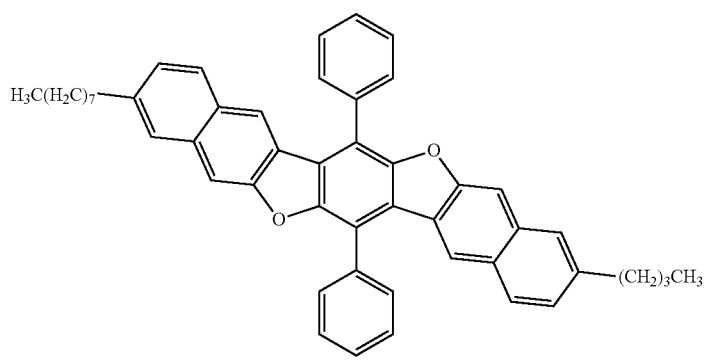
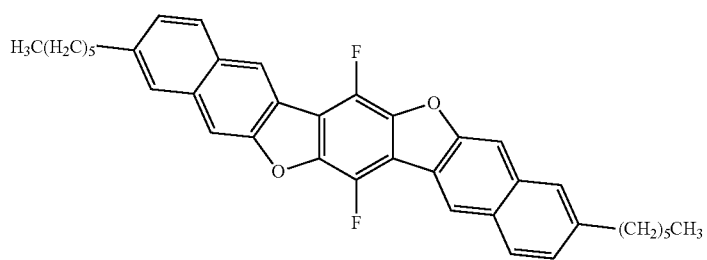

-continued
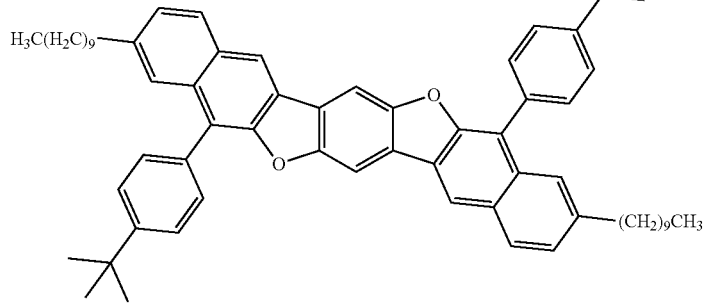
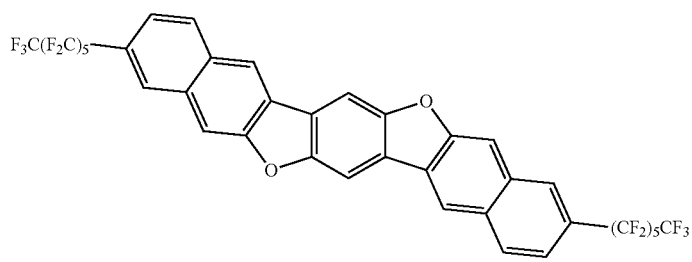
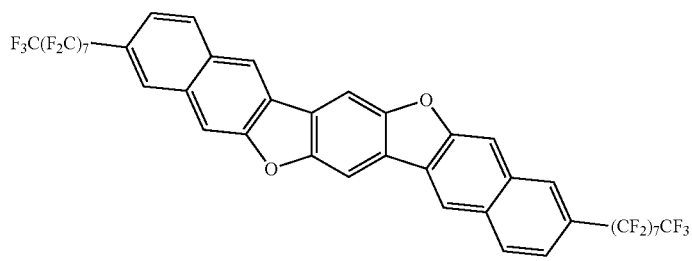
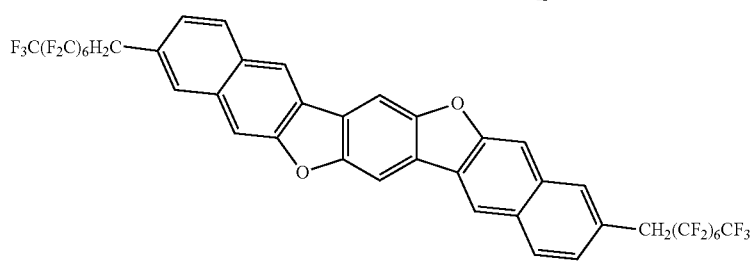
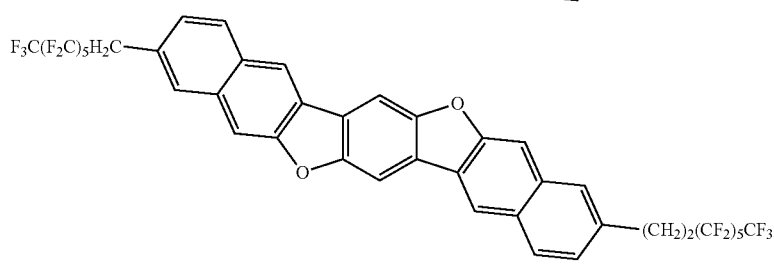
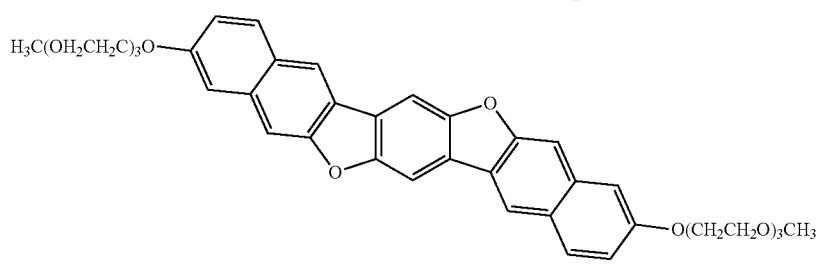

-continued
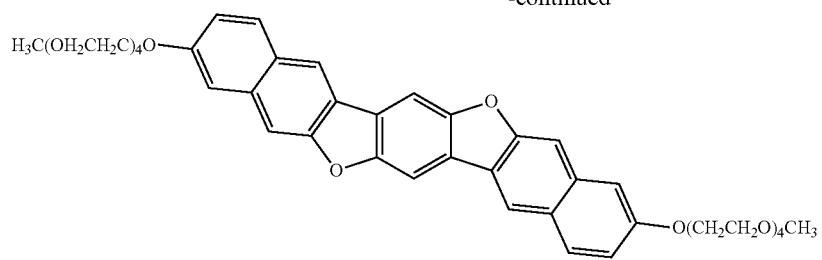
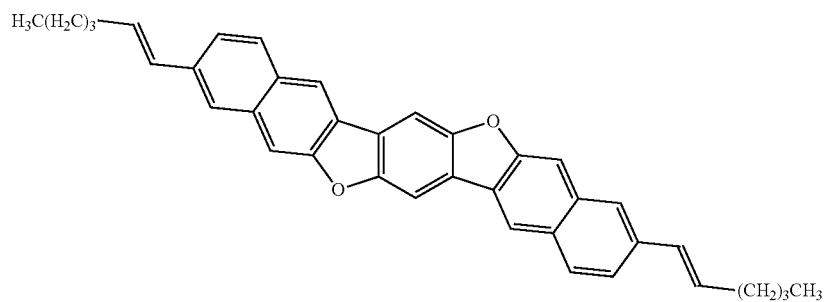
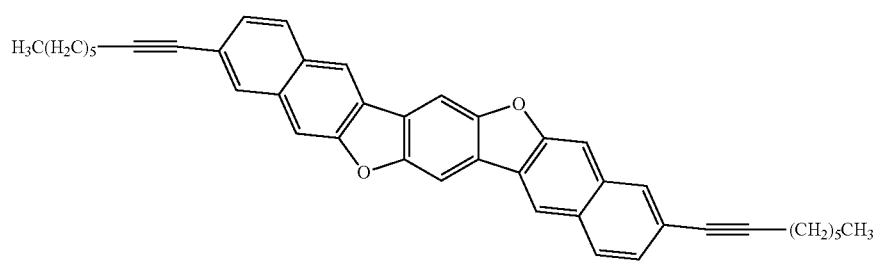
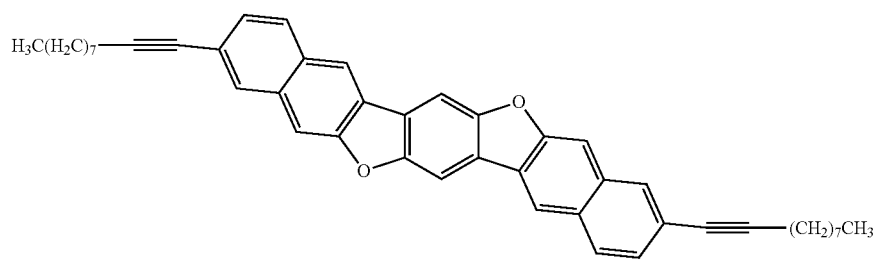
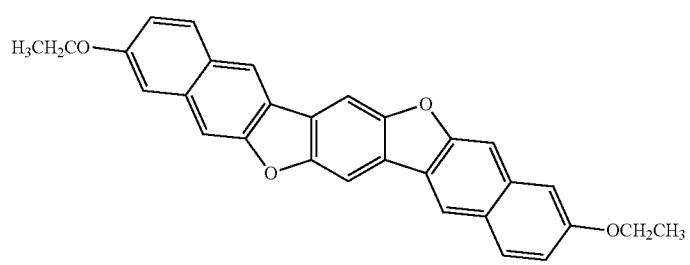
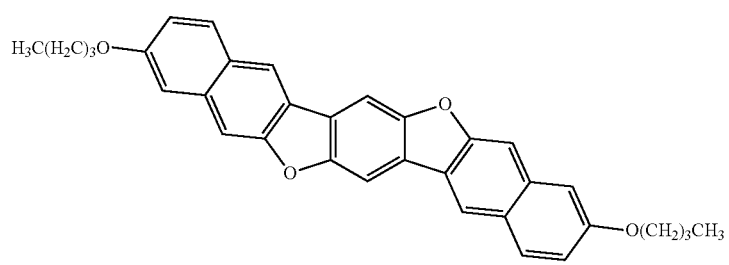

-continued
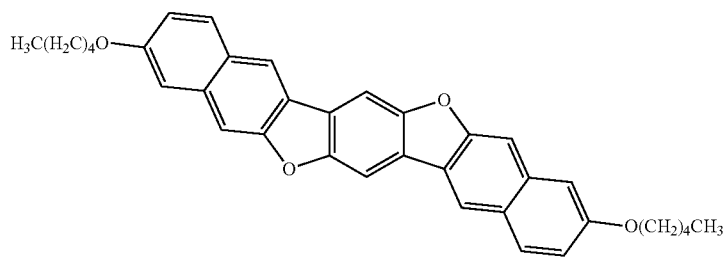
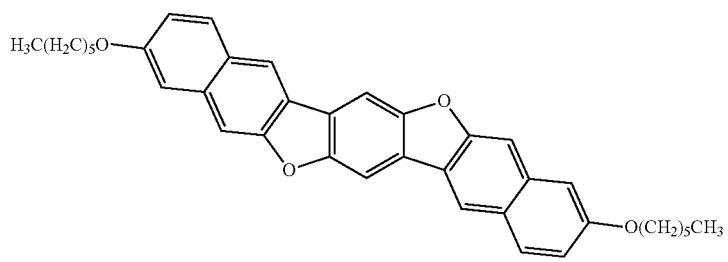
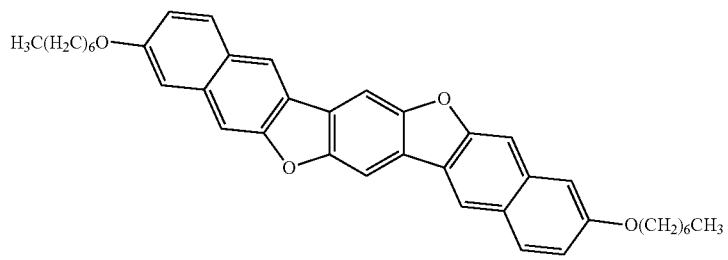
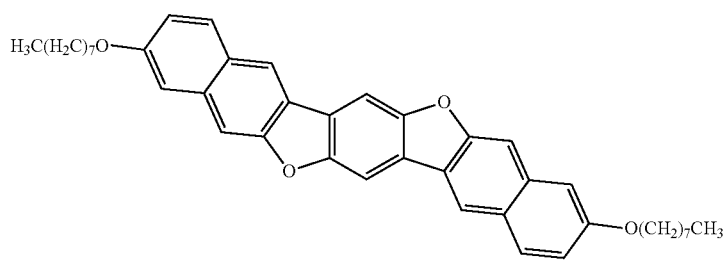
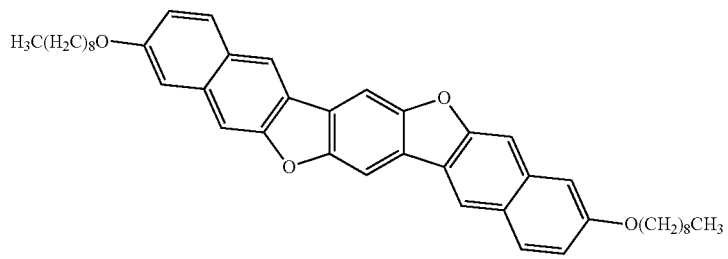
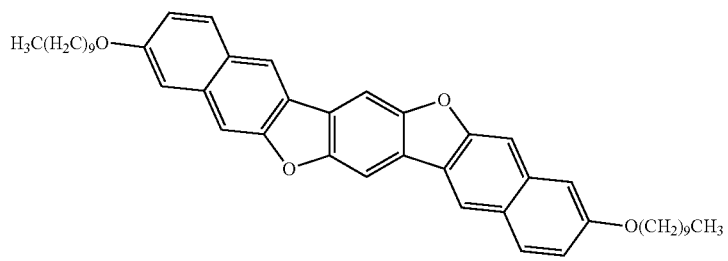

-continued
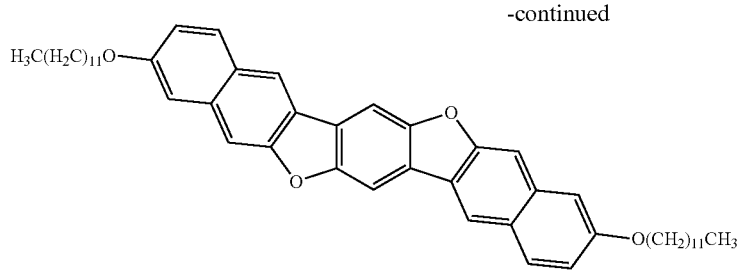
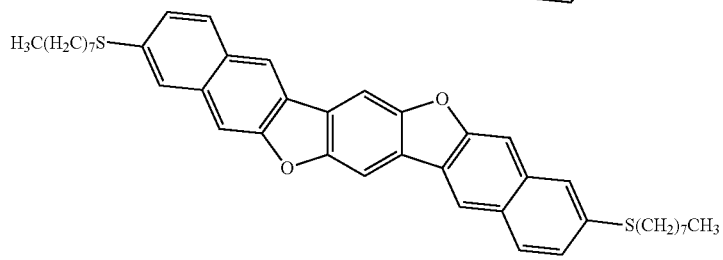
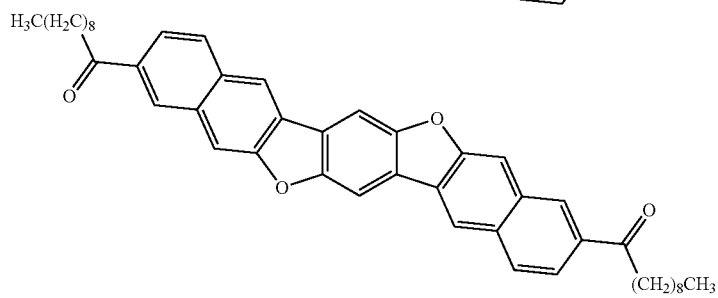
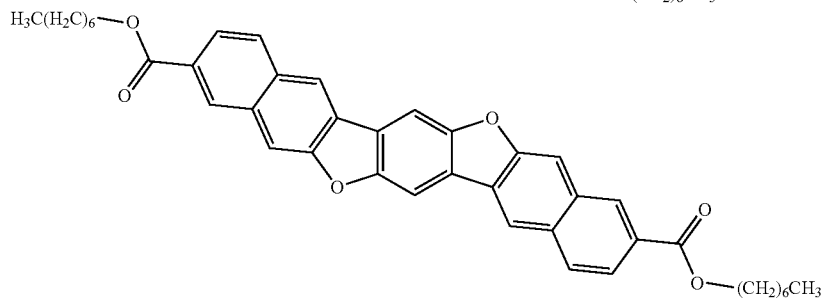
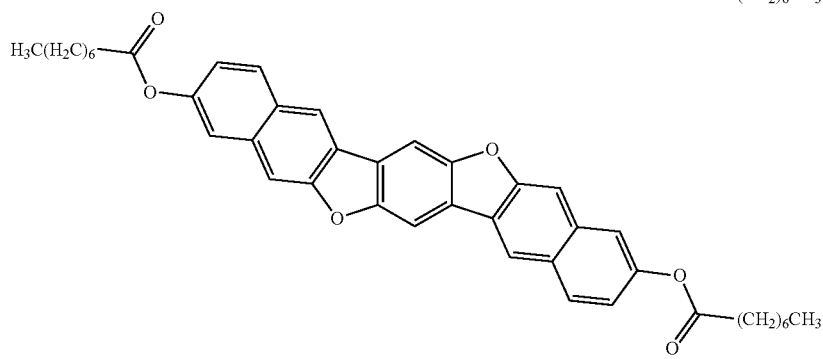
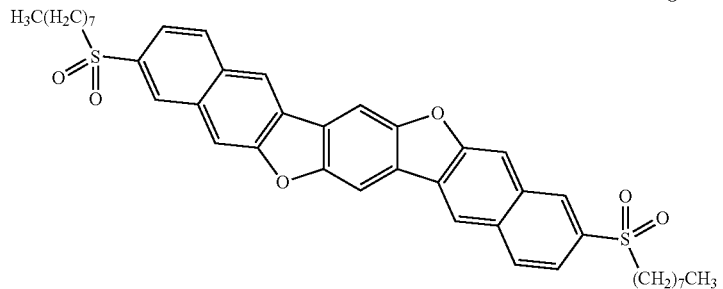

-continued
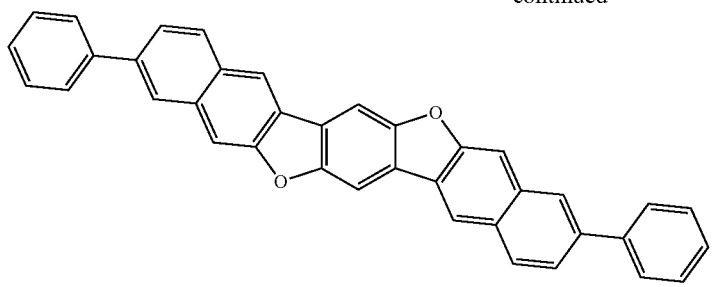
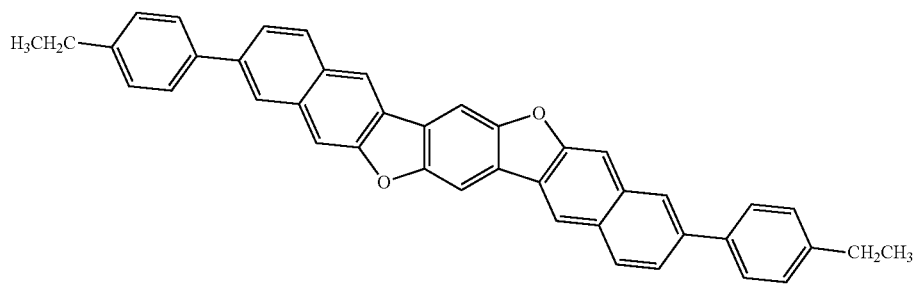
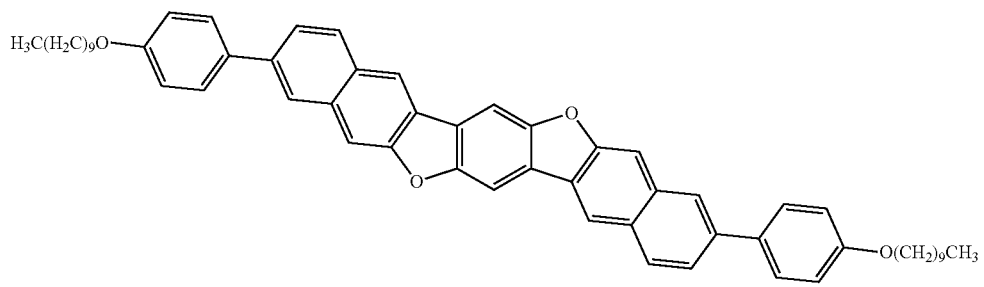
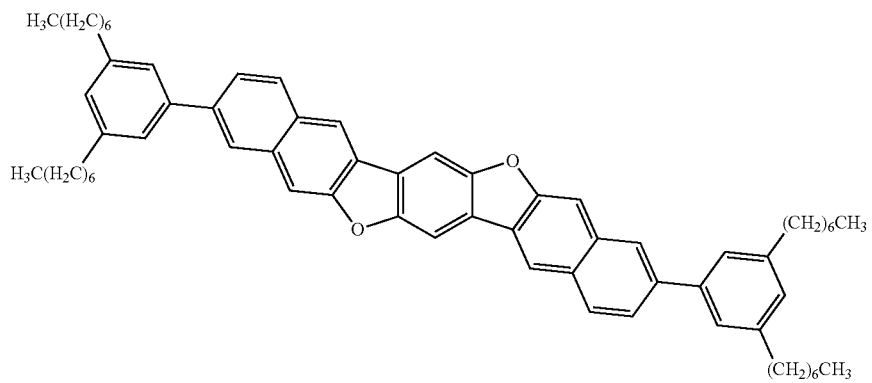
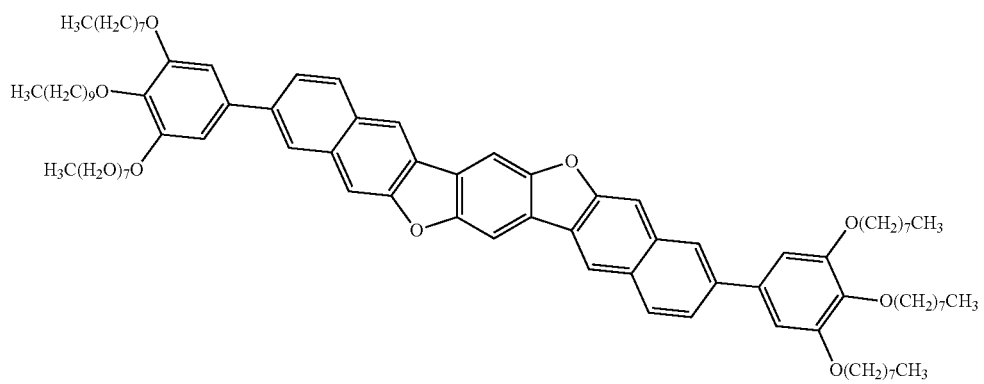

-continued
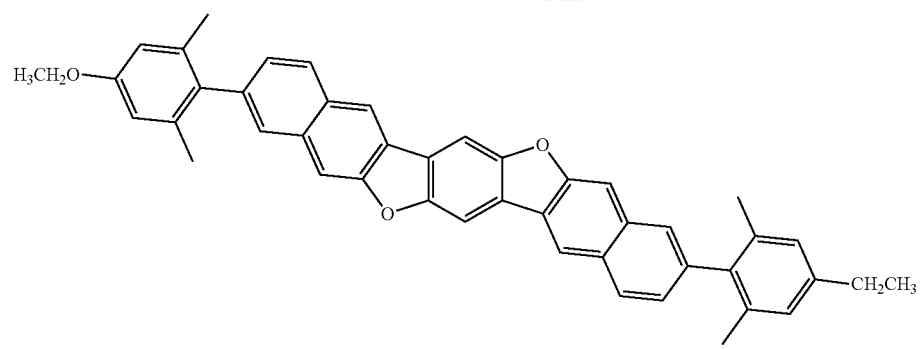
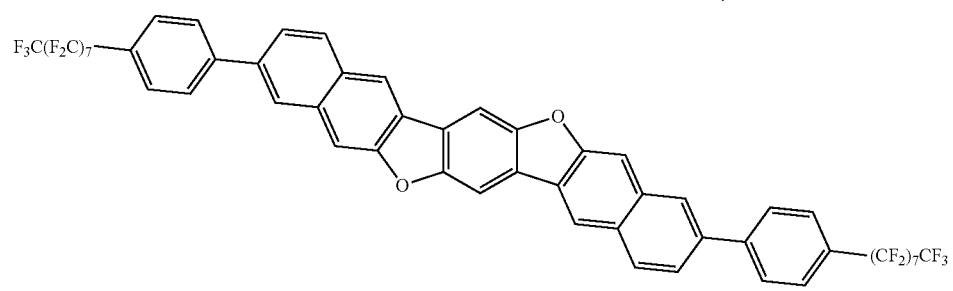
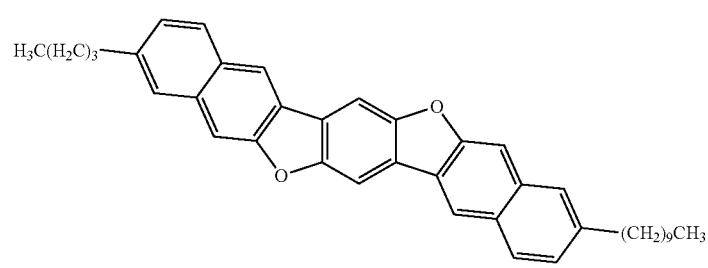
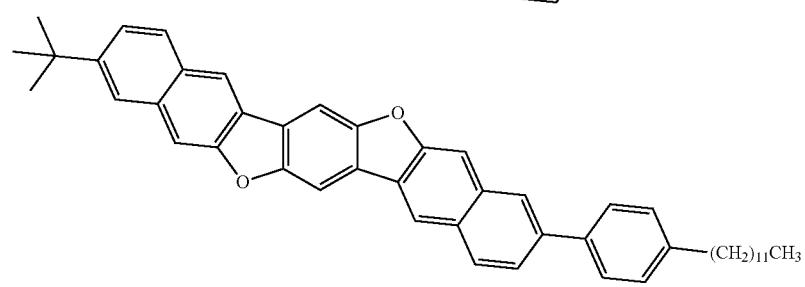
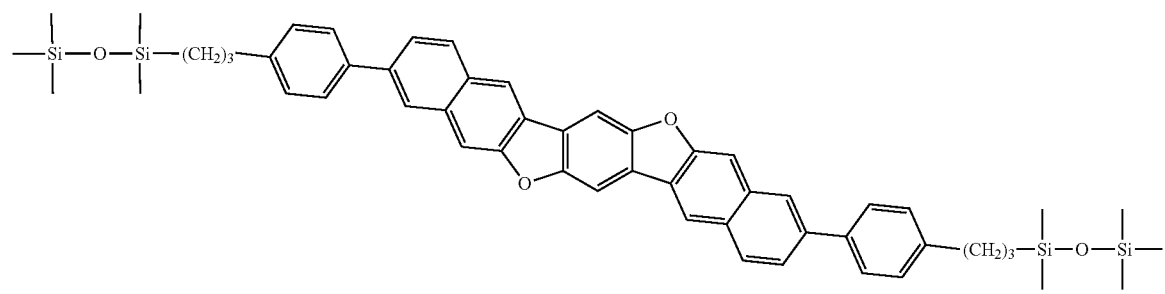
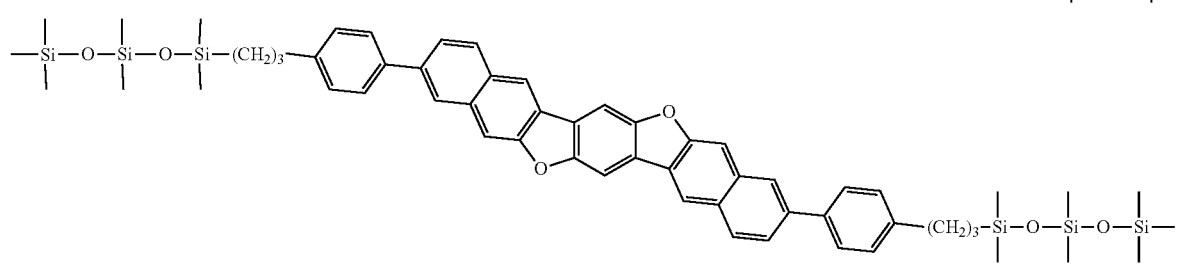

-continued
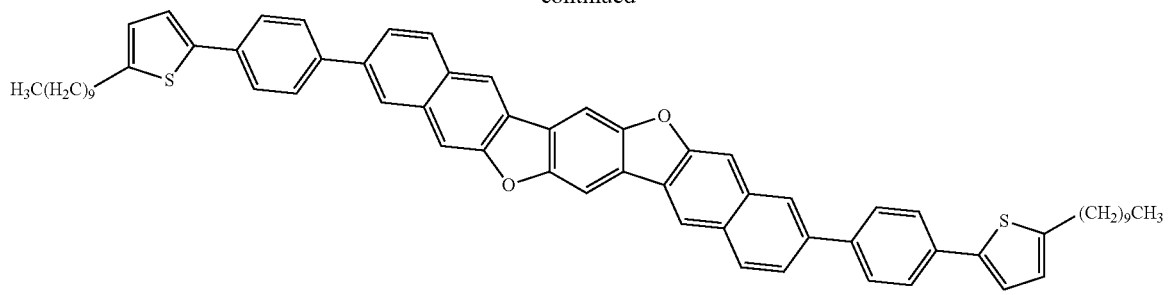
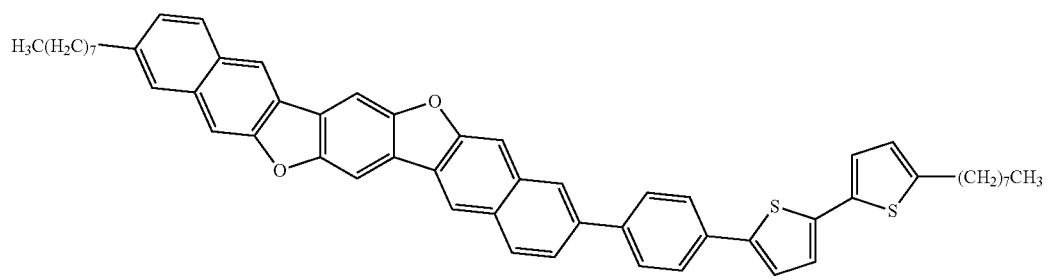
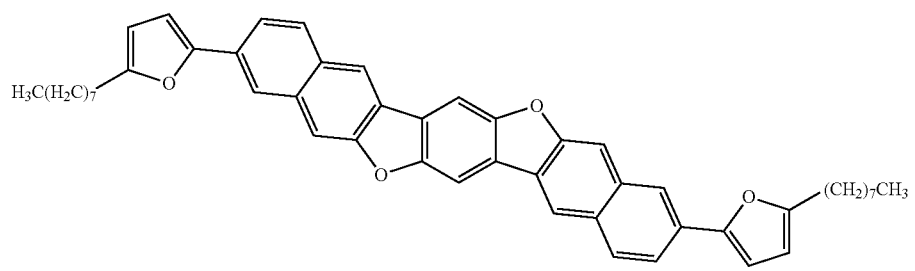
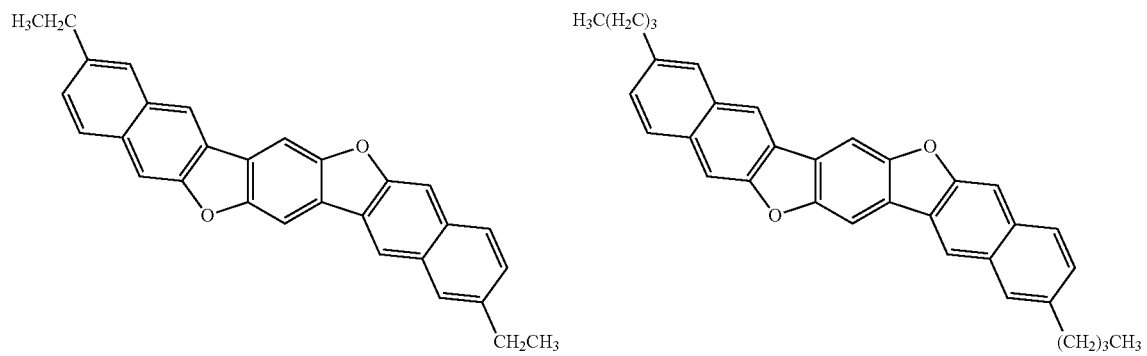
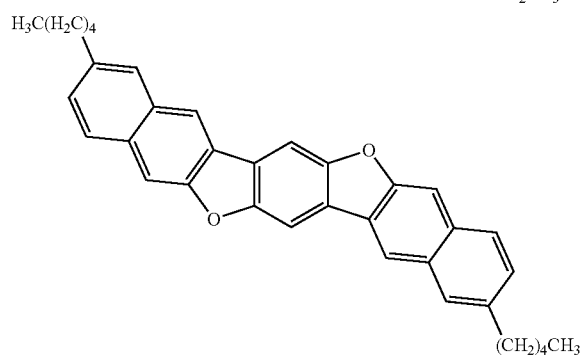

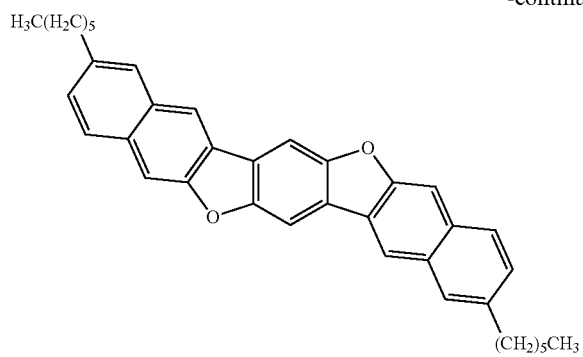
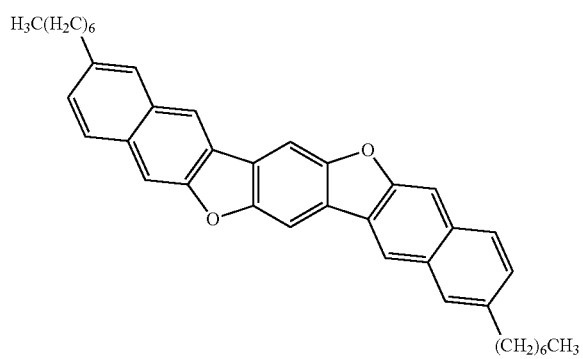
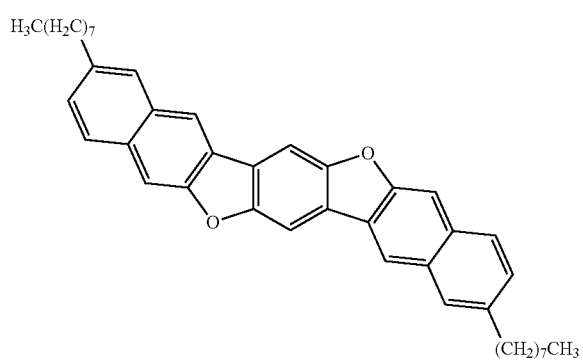
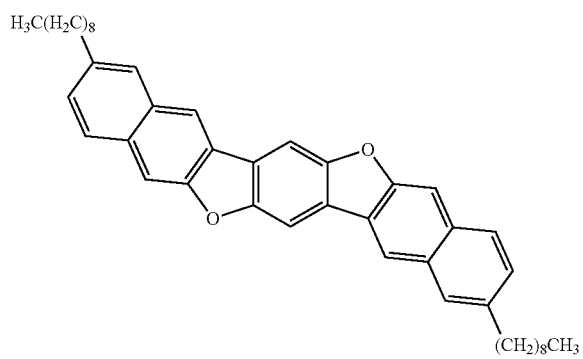

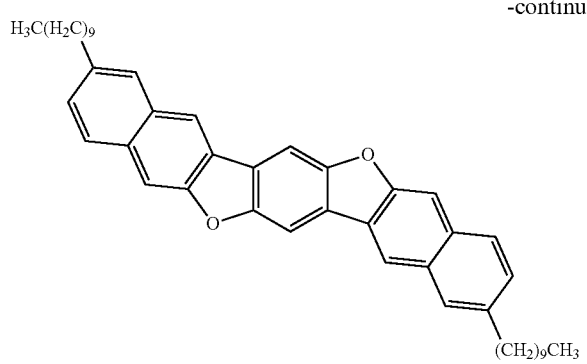
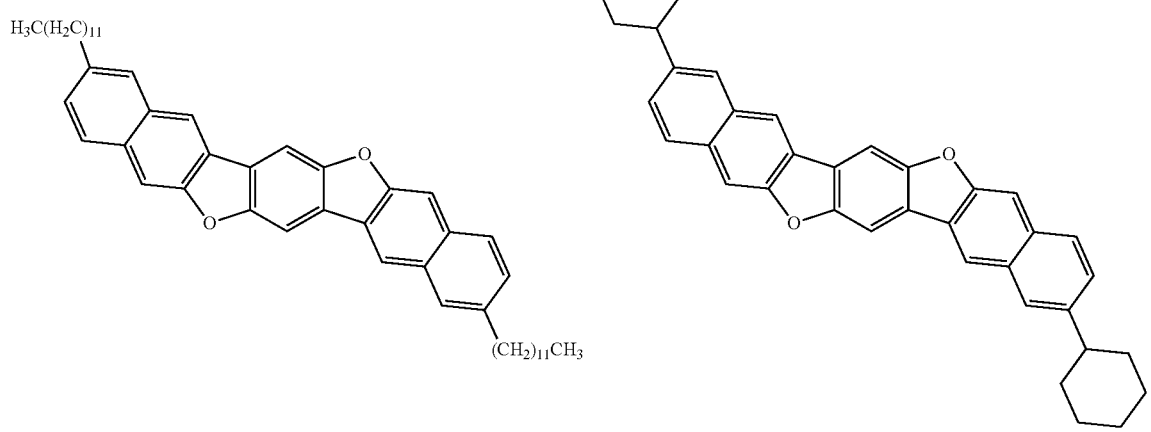
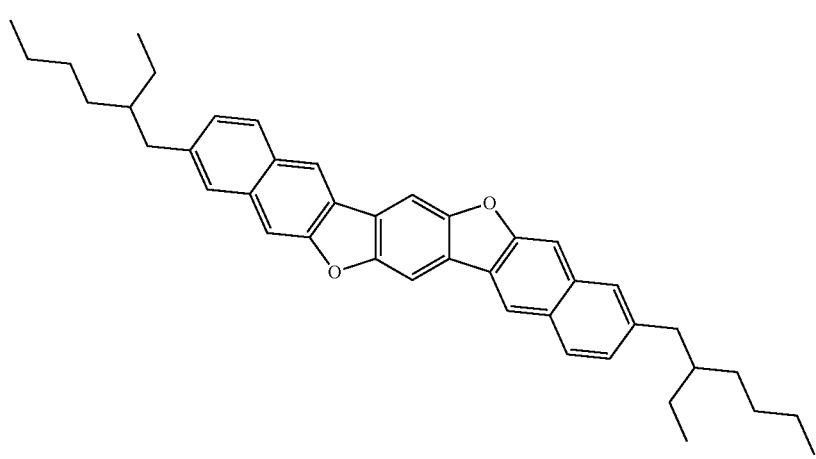
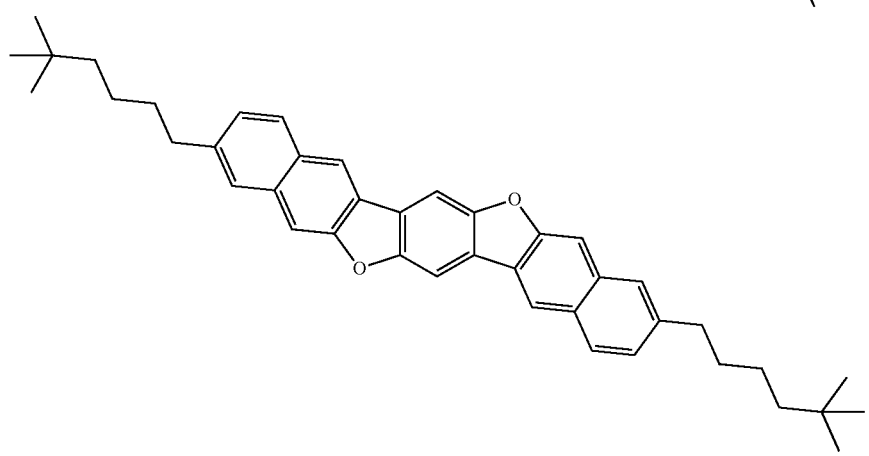

-continued
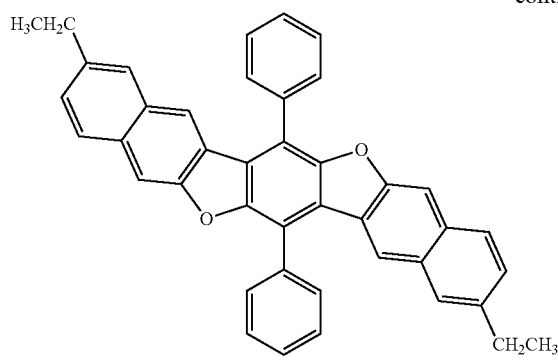
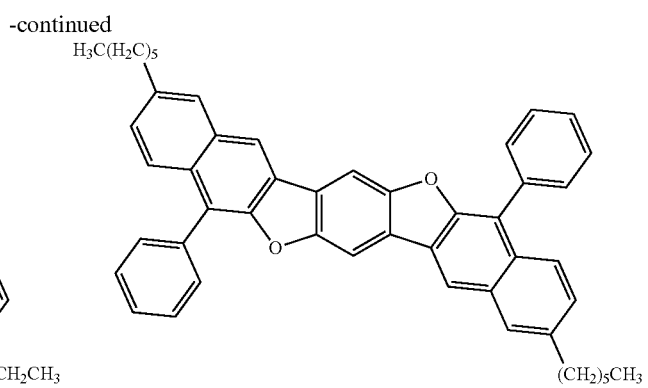
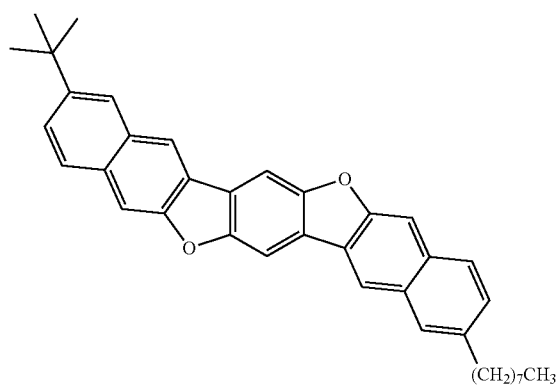
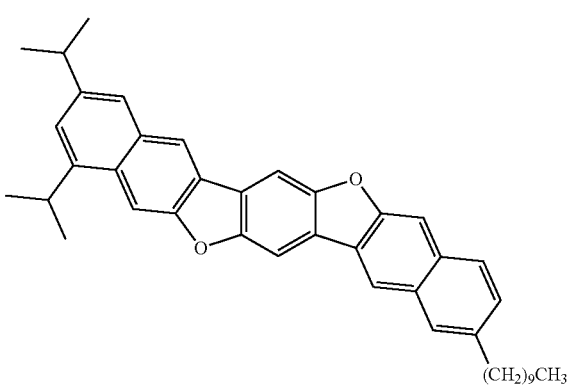
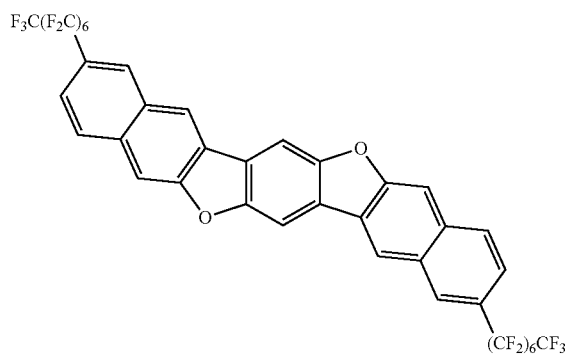
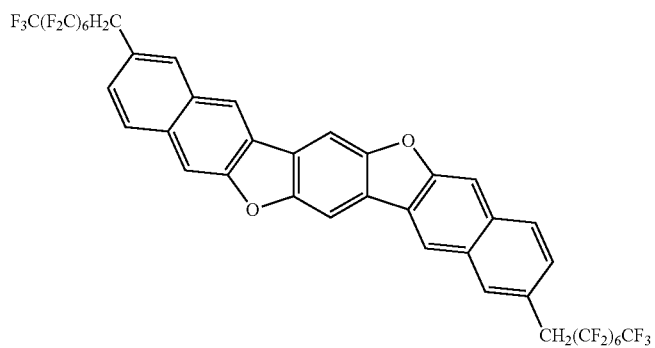

-continued
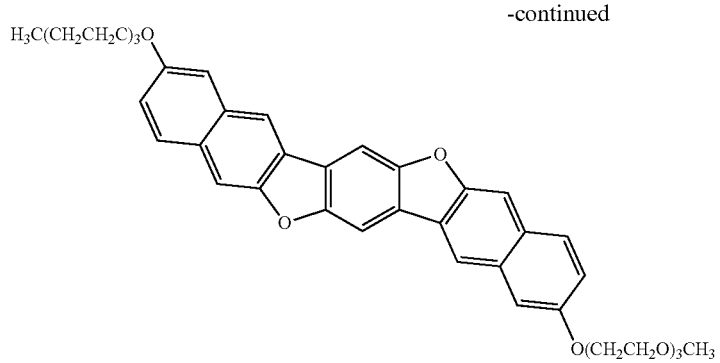
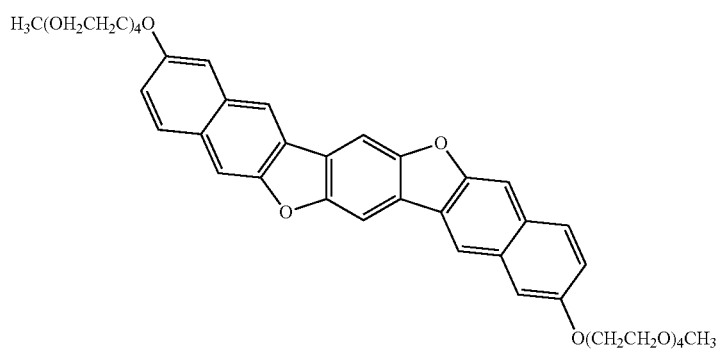
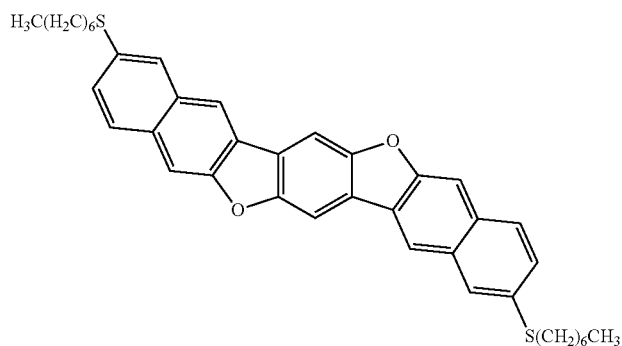
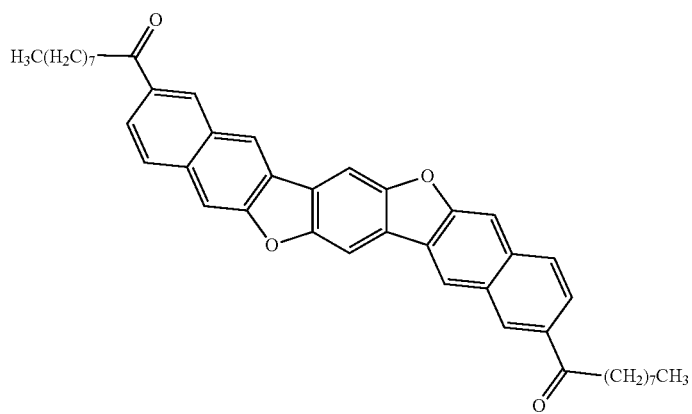

-continued
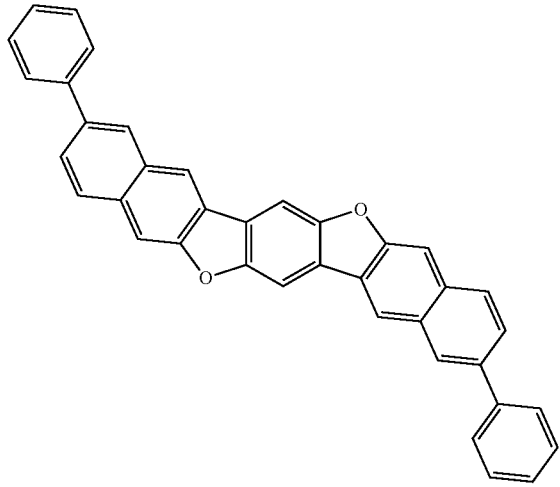
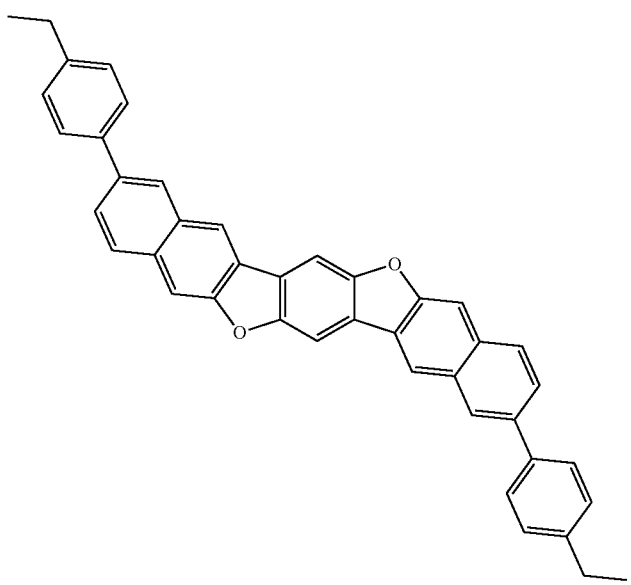
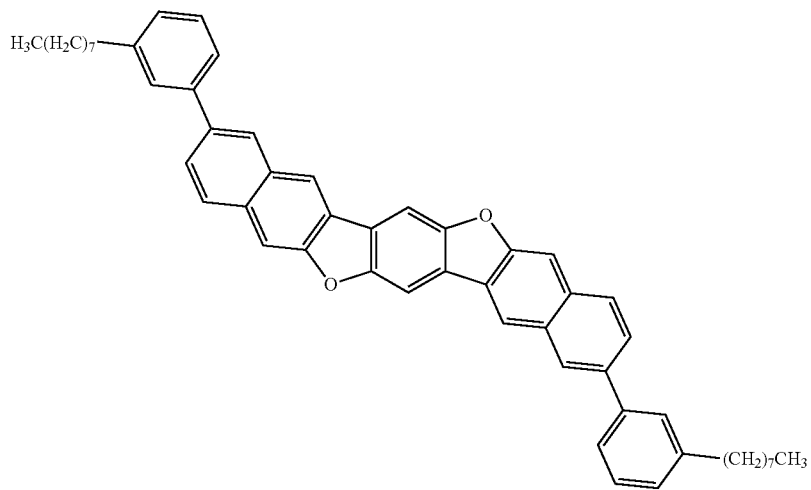

-continued
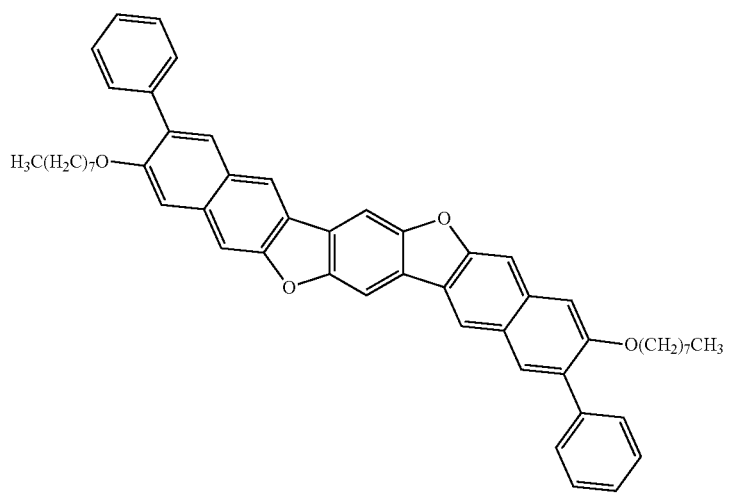
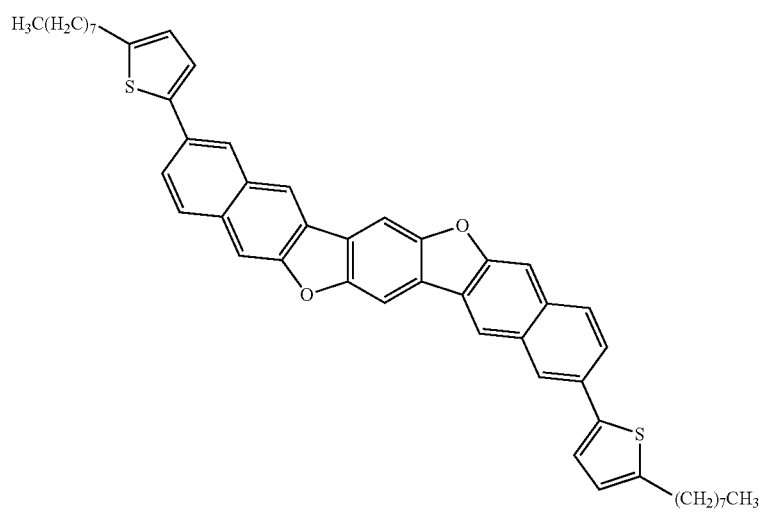
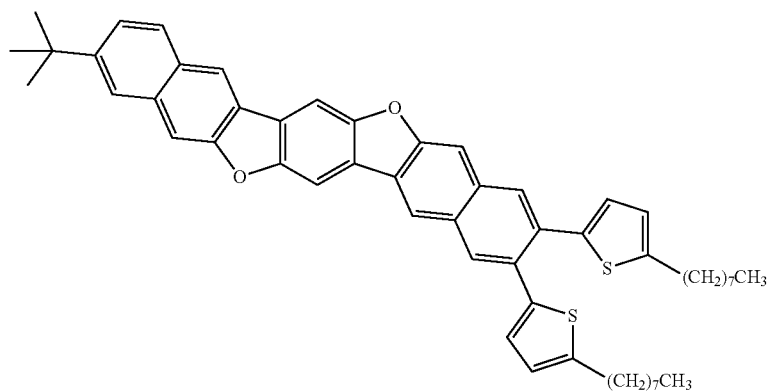

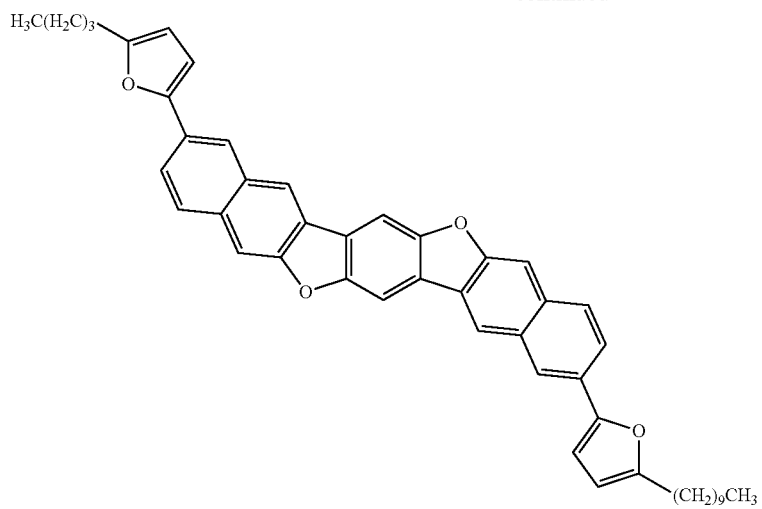
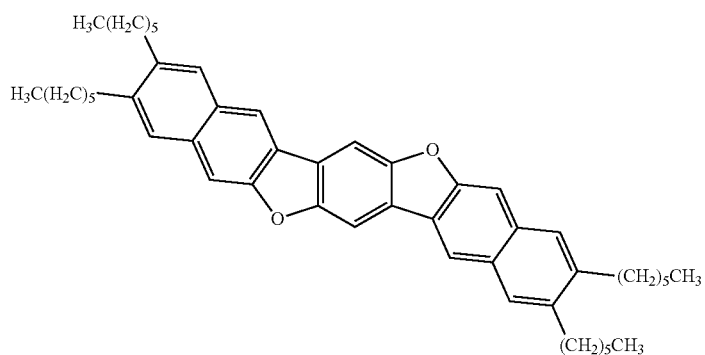
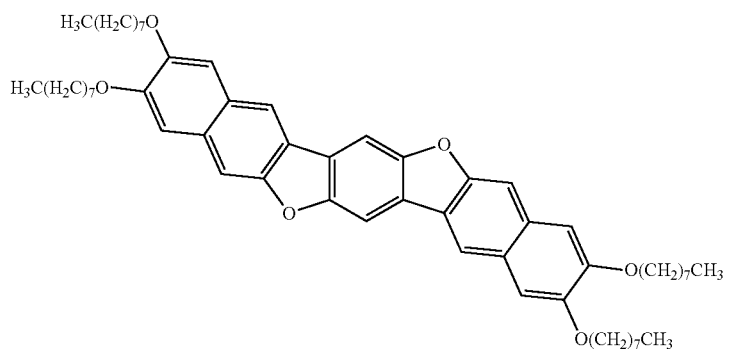
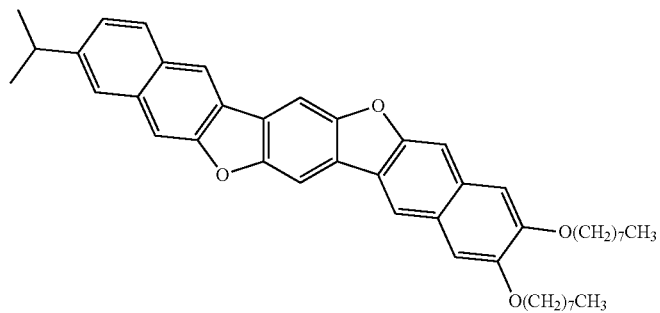

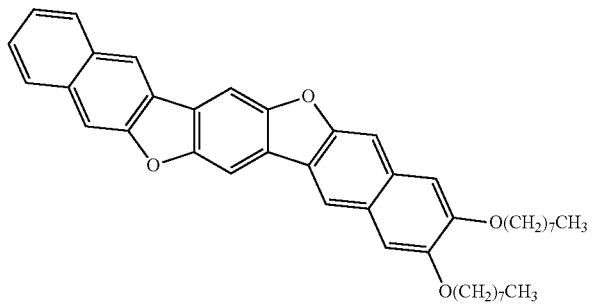
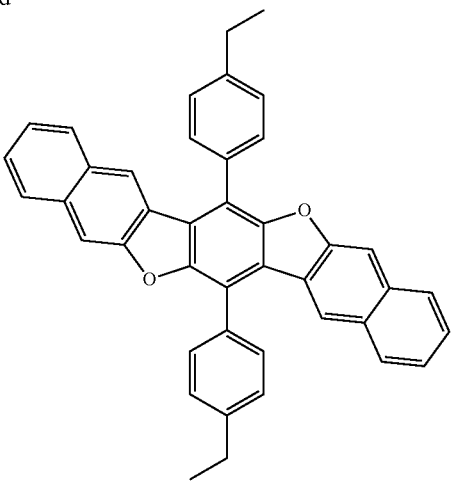
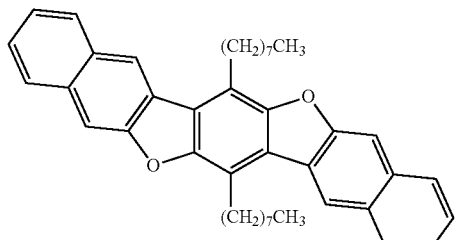
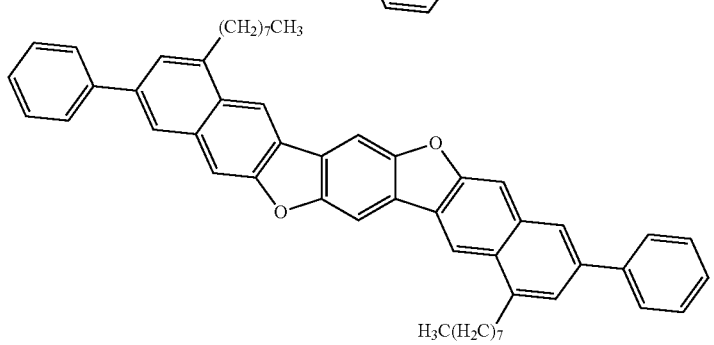
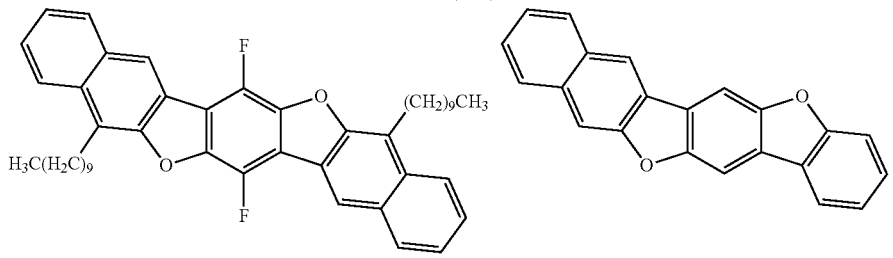
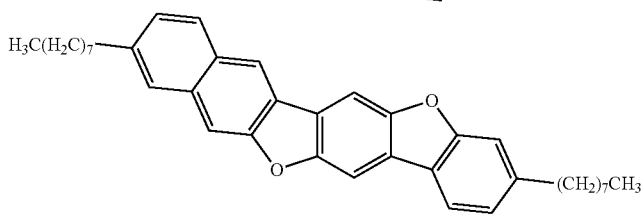
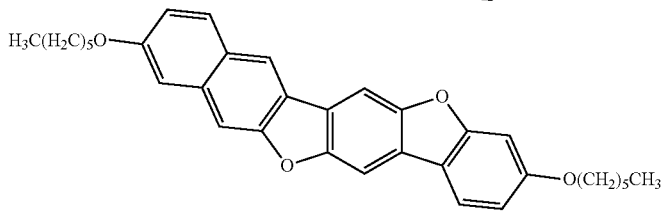

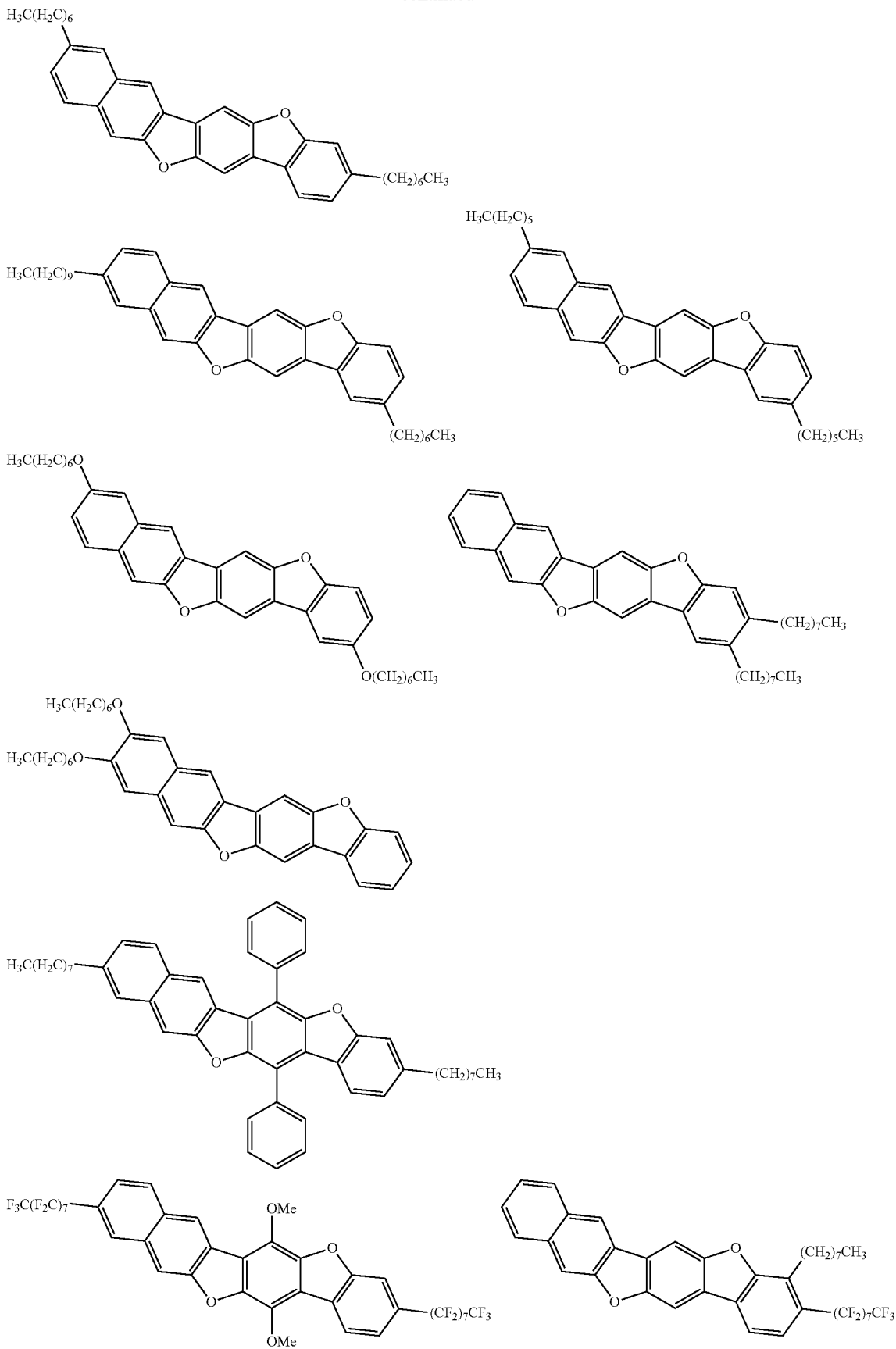

-continued
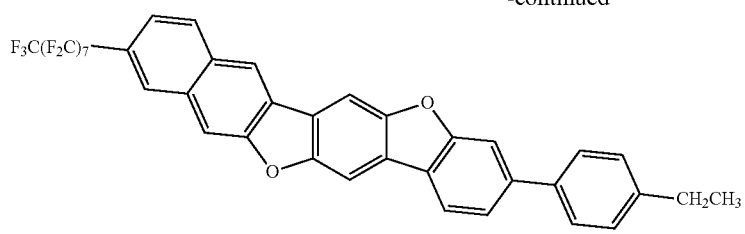
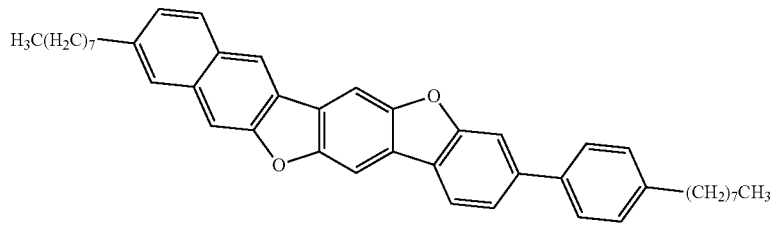
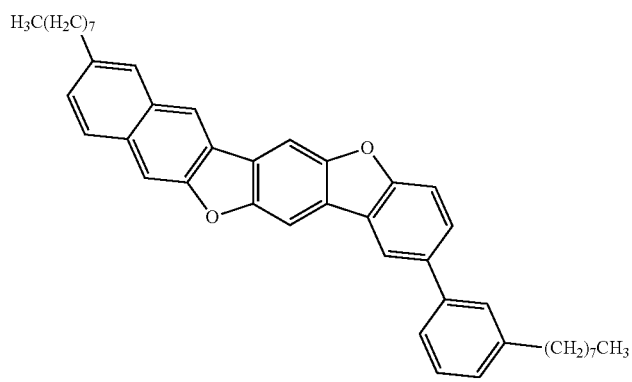
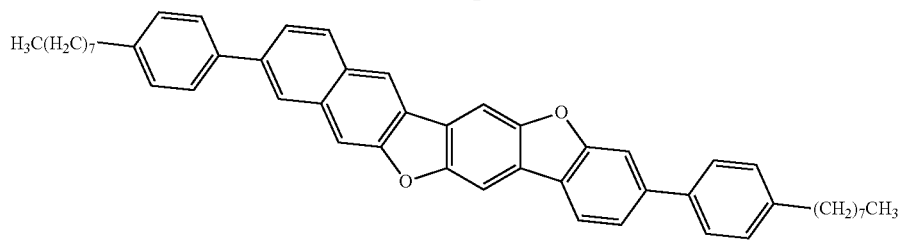
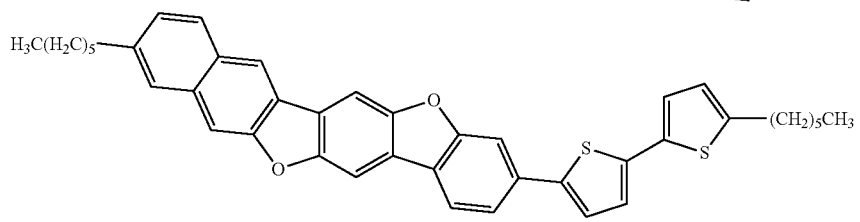
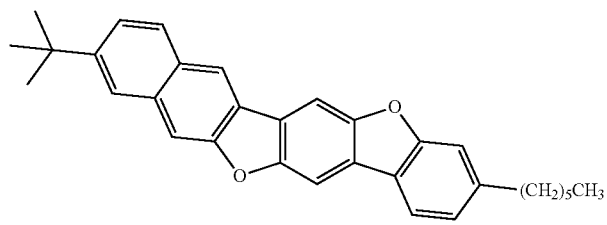
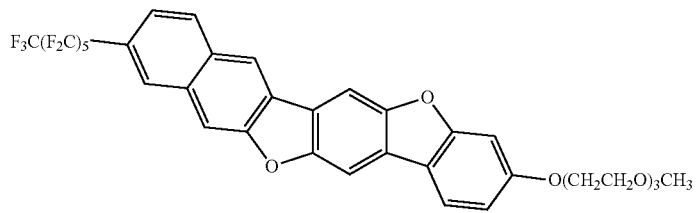

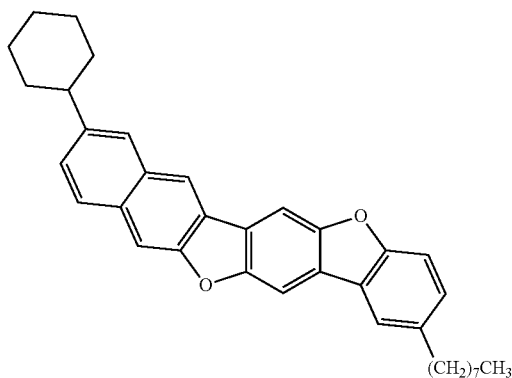
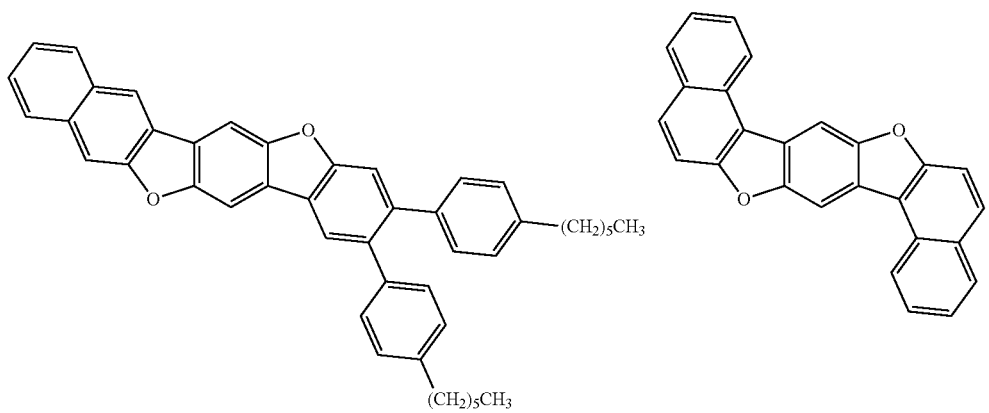
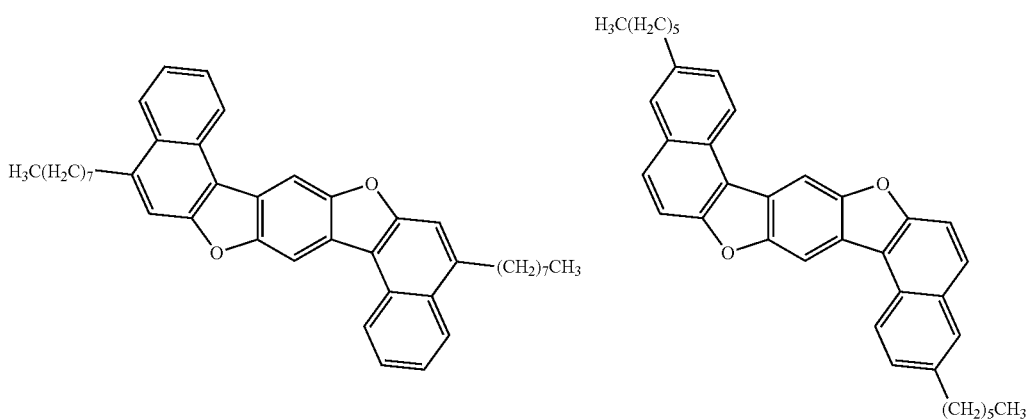
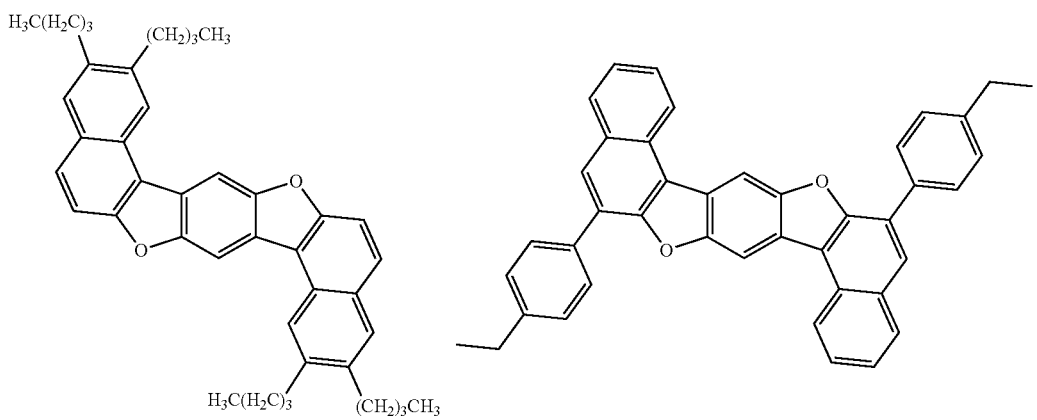

-continued
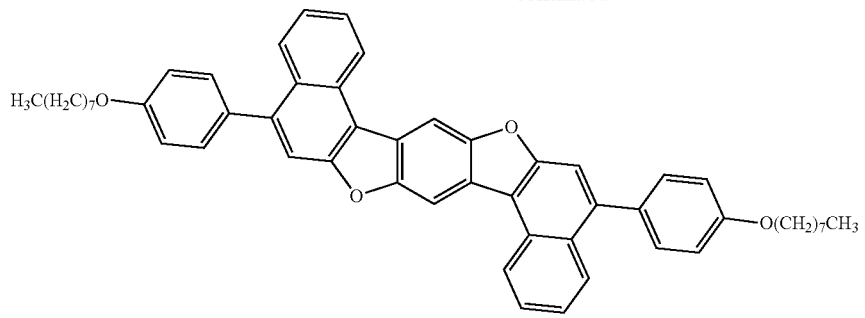
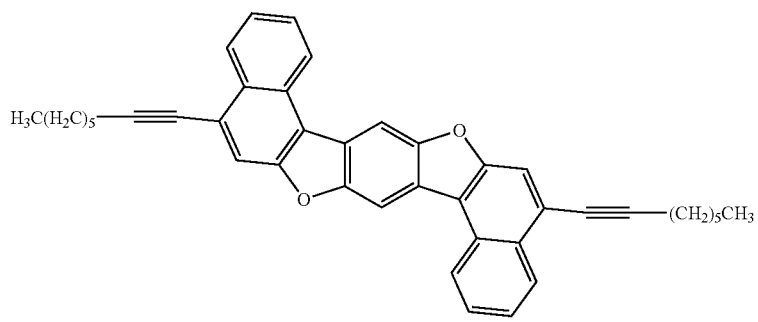
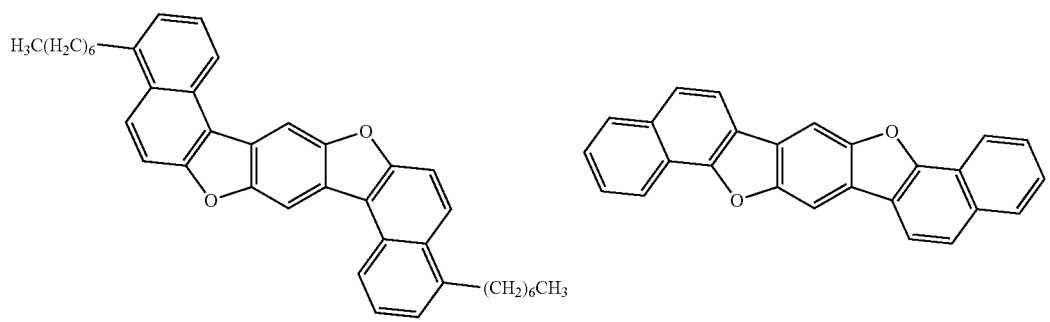
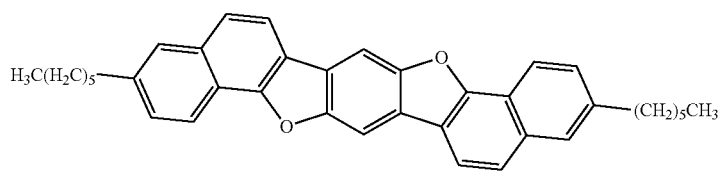
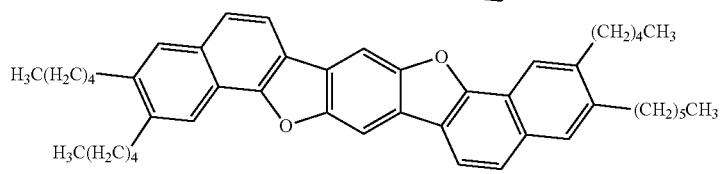
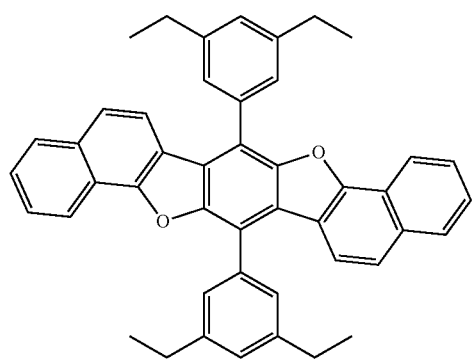

-continued
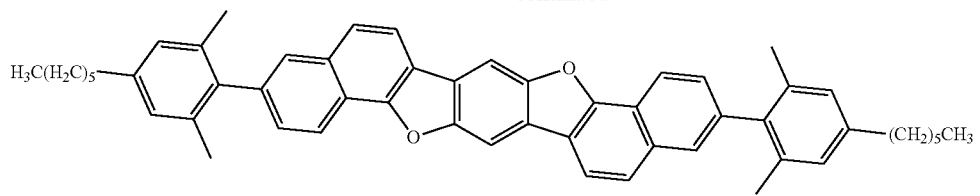
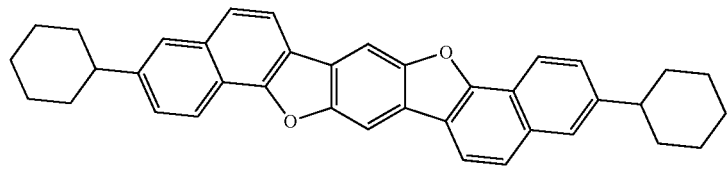
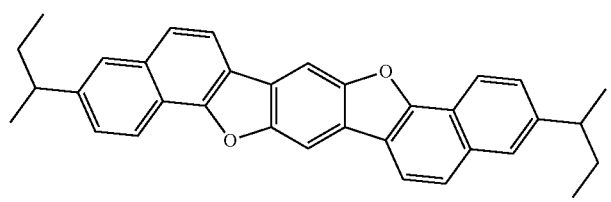
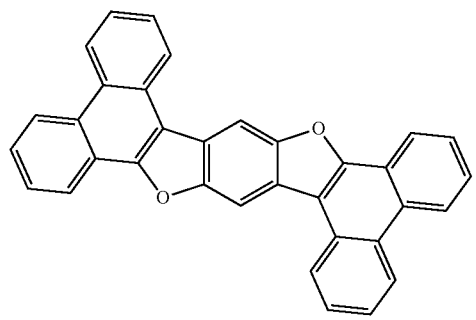
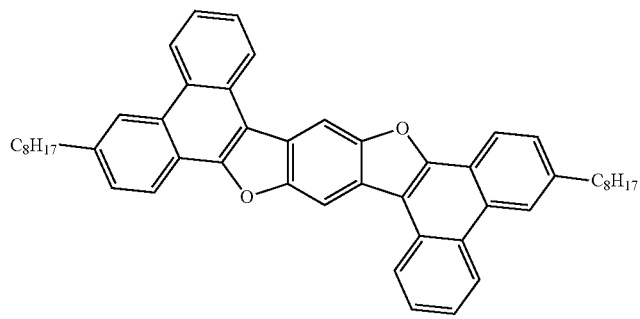
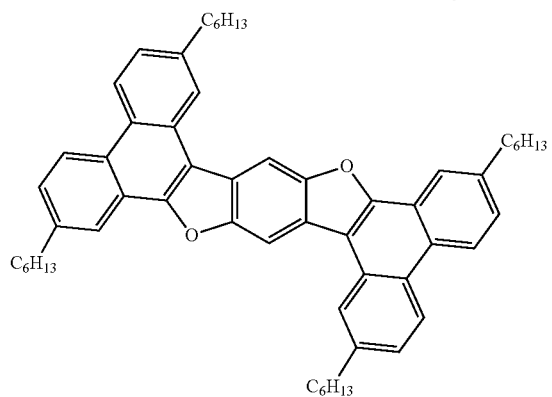
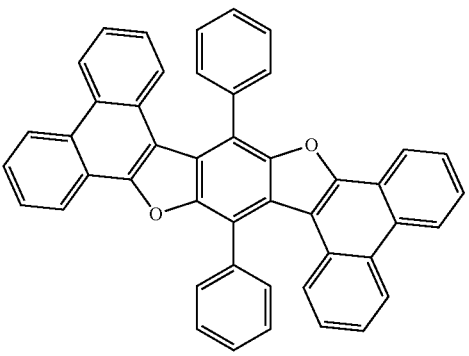

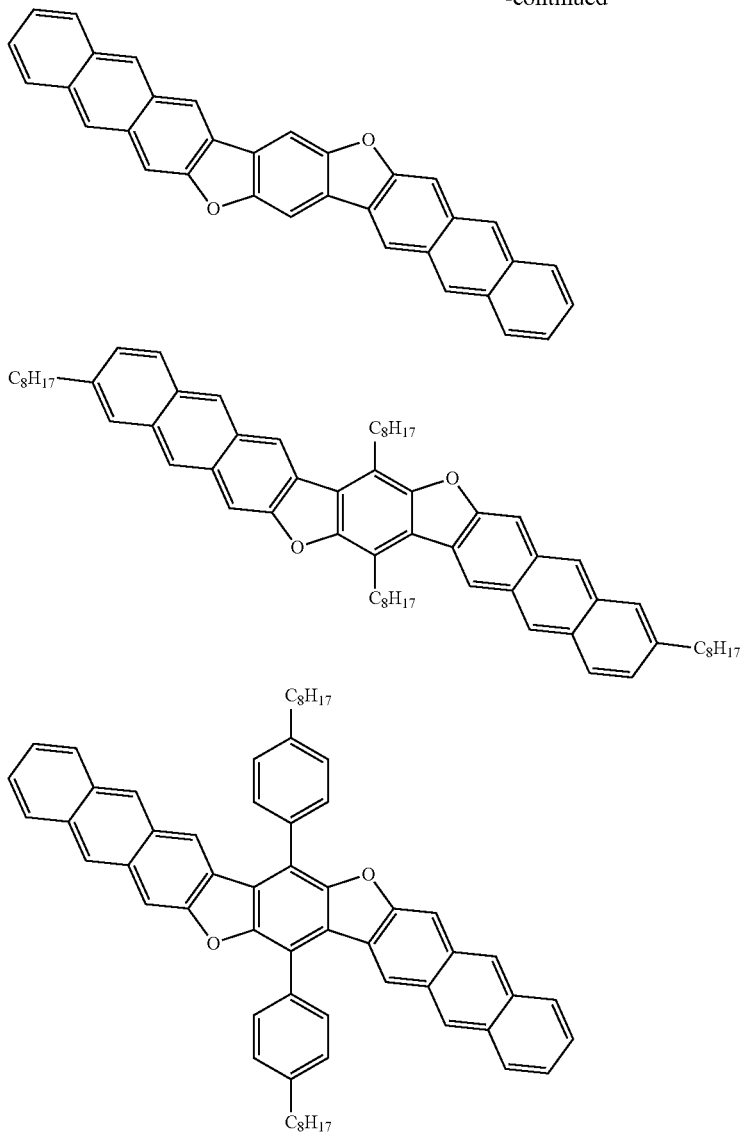

The compound represented by the general formula (1) preferably has a molecular weight of 3,000 or less, more preferably 2,000 or less, further preferably 1,000 or less, and particularly preferably 850 or less. The molecular weight thereof that is the upper limit or less is preferred since the solubility thereof in a solvent may be enhanced.

The molecular weight of the compound is preferably 400 or more, more preferably 450 or more, and further preferably 500 or more, from the standpoint of the stability of the film quality of the thin film.

The invention also relates to an organic semiconductor material for a non-light-emitting organic semiconductor device, a material for an organic thin film transistor, and a coating solution for a non-light-emitting organic semiconductor device, containing a compound represented by the general formula (1). The coating solution for a non-light-emitting organic semiconductor device may further contain a polymer binder. The non-light-emitting organic semiconductor device referred herein means a device that is not intended to emit light. The non-light-emitting organic semiconductor device encompasses an organic transistor, an organic photoelectric conversion device (such as a solid state image sensing device for an optical sensor, and a solar cell for energy conversion), a gas sensor, an organic rectifying device, an organic inverter, and an information recording device.

The invention also relates to an organic semiconductor thin film containing a compound represented by the general formula (1). The organic semiconductor thin film may further contain a polymer binder. The organic semiconductor thin film and the organic semiconductor thin film containing a polymer binder of the invention are preferably produced by a solution coating method.

The case where the organic semiconductor thin film that contains a polymer binder may be formed in such a manner that the materials for forming the layer and a polymer binder are dissolved or dispersed in a suitable solvent to form a coating liquid, which is then coated by a suitable coating method to form the thin film. Examples of the polymer binder include an insulating polymer, such as polystyrene, polycarbonate, polyarylate, polyester, polyamide, polyimide, polyurethane, polysiloxane, polysulfone, polymethyl methacrylate, polymethyl acrylate, cellulose, polyethylene and polypropylene, and copolymers thereof, a photoconductive polymer, such as polyvinylcarbazole and polysilane, and a conductive or semiconductive polymer, such as polythiophene, polypyrrole, polyaniline and poly-p-phenylenevinylene. The polymer binder may be used solely or as a combination of plural kinds thereof. The organic semiconductor material and the polymer binder may be mixed uniformly and may be entirely or partially phase-separated. A polymer binder having a high glass transition temperature is preferred from the standpoint of the mechanical strength of the thin film, and a polymer binder having a structure containing no polar group, a photoconductive polymer and a conductive polymer are preferred from the standpoint of the charge mobility. The amount of the polymer binder used is not particularly limited, and the polymer binder is preferably used in an amount in a range of from 5 to 95% by mass, more preferably from 10 to 90% by mass, further preferably from 20 to 80% by mass, and particularly preferably from 30 to 70% by mass, in the film formed of the compound of the invention.

The compound of the invention may have favorable capability as an organic semiconductor material even after storing under a high temperature and high humidity condition. For example, even after storing under a high temperature and high humidity condition, a high carrier mobility may be obtained, and the change in the mobility may be small. According to the capability, the organic thin film transistor of the invention may effectively function as a transistor under severe condition.

In the invention, furthermore, the change in the threshold voltage after high voltage operation or repeated operation may be small, and thereby the organic thin film transistor of the invention may exhibit good transistor characteristics for a prolonged period of time.

In the invention, moreover, the compound has the aforementioned structure and thus may provide an organic thin film having good film quality. The compound obtained in the invention may have good crystallinity and thus may provide a sufficient film thickness, and the resulting film may have good quality. In the invention, a high carrier mobility may be obtained due to the good crystallinity, thereby providing excellent transistor characteristics.

Synthesis Method

The compound represented by the general formula (1) may be synthesized by combining the known reactions. For example, the compound may be synthesized, for example, by referring to Molecular Electronics and Bioelectronics, The Japan Society of Applied Physics, vol. 22, pp. 9-12 (2011), WO 2009/148016, and the like.

The benzobisnaphthofuran ring forming reaction in the invention may be performed in any kind of reaction conditions. The reaction solvent used may be any solvent. An acid or a base is preferably used for accelerating the ring forming reaction, and a base is particularly preferably used therefor. The optimum reaction conditions may vary depending on the structure of the target benzobisnaphthofuran derivative and may be determined by referring to the specific reaction conditions shown in the aforementioned literatures.

A synthetic intermediate having various substituents may be synthesized by combining the known reactions. The substituents may be introduced in any of the stages of intermediates. The intermediate after synthesis is preferably purified by column chromatography, recrystallization and the like, and then further purified by sublimation purification. The sublimation purification not only isolates organic impurities but also effectively removes inorganic salts, residual solvents and the like.

Organic Semiconductor Material

The organic semiconductor material in the invention means an organic material that exhibits characteristics of a semiconductor. The organic semiconductor material includes a p-type (hole transporting) organic semiconductor conducting holes as a carrier and an n-type (electron transporting) organic semiconductor conducting electrons as a carrier, as similar to a semiconductor formed of an inorganic material. The compound of the invention may be used as any of a p-type organic semiconductor material and an n-type organic semiconductor material, and is more preferably used as a p-type organic semiconductor material. The degree of ease of a carrier passing in an organic semiconductor is expressed by a carrier mobility $\mu$. The carrier mobility $\mu$ is preferably larger, and is preferably $1 \times 10^{-3}$ cm$^2$/Vs or more, and more preferably $1 \times 10^{-2}$ cm$^2$/Vs or more. The carrier mobility $\mu$ may be obtained from the characteristics of a field effect transistor (FET) device formed with the material or by a time-of-flight (TOF) method.

Film Formation Method

The compound of the invention may be formed into a film on a substrate in any method, and may be formed into a film by any of a vacuum process and a solution process, both of which are preferred. Specific examples of the film formation by a vacuum process include a physical vapor phase epitaxial method, such as a vacuum vapor deposition method, a sputtering method, an ion plating method and a molecular beam epitaxial (MBE) method, and a chemical vapor phase deposition (CVD) method, such as a plasma polymerization method, and a vacuum vapor deposition method is particularly preferably used. The film formation by a solution process herein means that the organic compound is dissolved in a solvent that is capable of dissolving the compound to form a solution, and the film is formed by using the solution. Any ordinary methods may be used, examples of which include a coating method, such as a casting method, a dip coating method, a die coater method, a roll coater method, a bar coater method and a spin coating method, a printing method, such as an inkjet method, a screen printing method, a gravure printing method, a flexography printing method, an offset printing method and a microcontact printing method, and a Langmuir-Blodgett (LB) method, and a casting method, a spin coating method, an ink jet method, a gravure printing method, a flexography printing method, an offset printing method and a microcontact printing method are particularly preferably used.

Coating Conditions

In the case where the thin film is formed on a substrate by a solution process, the materials for forming layer may be dissolved in a suitable organic solvent and/or water to form a coating liquid, which may be then coated by a suitable coating method to form the thin film. Examples of the organic solvent include a hydrocarbon solvent, such as hexane, octane, decane, toluene, xylene, mesitylene, ethylbenzene, decalin and 1-methylnaphthalene, a ketone solvent, such as acetone, methyl ethyl ketone, methyl isobutyl ketone and cyclohexanone, a halogenated hydrocarbon solvent, such as dichloromethane, chloroform, tetrachloromethane, dichloroethane, trichloroethane, tetrachloroethane, chlorobenzene, dichlorobenzene and chlorotoluene, an ester solvent, such as ethyl acetate, butyl acetate and amyl acetate, an alcohol solvent, such as methanol, propanol, butanol, pentanol, hexanol, cyclohexanol, methyl cellosolve, ethyl cellosolve and ethylene glycol, an ether solvent, such as dibutyl ether, tetrahydrofuran, dioxane and anisole, an amide or imide solvent, such as N,N-dimethylformamide, N,N-dimethylacetamide, 1-methyl-2-pyrrolidone and 1-methyl-2-imidazolidinone, a sulfoxide solvent, such as dimethylsulfoxide, and a nitrile solvent, such as acetonitrile. The solvent may be used solely or as a combination of plural kinds thereof. The concentration of the compound represented by the general formula (1) in the coating liquid is preferably from 0.1 to 80% by mass, and more preferably from 0.1 to 10% by mass, and thereby a film having an arbitrary thickness may be formed.

For forming the film by a solution process, it is necessary to dissolve the materials in the solvent, and it is insufficient that the materials are simply dissolved in the solvent. In general, materials that are formed into a film by a vacuum process may also be dissolved in a solvent to a certain extent. In a solution process, however, after the materials are dissolved in a solvent and then coated, such a process step is necessarily performed that the solvent is evaporated to form a thin film, and a material that is not suitable for a solution process often has high crystallinity and thus is inappropriately crystallized (aggregated) in the process step, so as to fail to provide a favorable thin film. The compound represented by the general formula (1) may be advantageously prevented from undergoing the crystallization (aggregation).

A polymer binder may be used in the formation of the film. In this case, the materials for forming layer and the polymer binder are dissolved or dispersed in the aforementioned suitable solvent to form a coating liquid, which is then coated by a suitable coating method to form the thin film. The polymer binder used may be selected from those described above.

In the formation of the film, the substrate may be heated or cooled, and the film quality and the molecular packing in the film may be controlled by changing the temperature of the substrate. The temperature of the substrate is not particularly limited and is preferably from 0 to 200° C.

Description of Electronic Device

The electronic device used in the invention may be any device, and is preferably a non-light-emitting device that uses an electronic element having a layer structure formed of thin films. Examples of the non-light-emitting organic electronic device using the electronic element of the invention include an organic transistor, an organic photoelectric conversion device, a gas sensor, an organic rectifying device, an organic inverter, and an information recording device. The organic photoelectric conversion device may be used for both photosensing (e.g., a solid state image sensing device) and energy conversion (e.g., a solar cell). Preferred examples of the non-light-emitting organic electronic device include an organic photoelectric conversion device and an organic transistor, and more preferred examples thereof include an organic transistor. Accordingly, a preferred embodiment thereof will be described with reference to the drawing, but the invention is not limited to the embodiment.

Device Structure of Field Effect Transistor

FIG. 1 is a cross sectional view schematically showing a structure of an organic field effect transistor using the electronic element of the invention. The transistor shown in FIG. 1 has a laminated structure as a basic structure, in which a substrate 11 (for example, a polyester film, such as polyethylene naphthalate (PEN) and polyethylene terephthalate (PET), a cycloolefin polymer film, a polycarbonate film, a triacetyl cellulose (TAC) film, a polyimide film, and a film containing the polymer film laminated on an ultrathin glass film, and ceramics, silicon, quartz, and glass, and the like) is disposed as the lowermost layer, an electrode 12 is provided on a part of the upper surface of the substrate 11, and an insulator layer 13 is disposed in such a manner that the insulator layer 13 is in contact with the substrate in the area except for the electrode. An organic semiconductor layer 14 is provided on the upper surface of the insulator layer 13, and two electrodes 15a and 15b are provided on a part of the upper surface of the organic semiconductor layer 14 in such a manner that the electrodes are separated from each other. The material constituting the electrode 12 and the electrodes 15a and 15b may be any known conductive material without particular limitation, examples of which include a metal, such as Cr, Al, Ta, Mo, Nb, Cu, Ag, Au, Pt, Pd, In, Ni and Nd, an alloy thereof, a carbon material, and a conductive polymer. The structure shown in FIG. 1 is referred to as a bottom-gate top-contact device, and a bottom-gate bottom-contact device, in which electrodes 15a and 15b are disposed in a lower part of an organic semiconductor layer, and a top-gate top-contact device and a top-gate bottom-contact device, in which an insulator 13 and a gate electrode 12 are disposed in an upper part of an organic semiconductor layer, may also be preferably used.

The gate width (or the channel width) W and the gate length (or the channel length) L are not particularly limited, and the ratio thereof W/L is preferably 10 or more, and more preferably 20 or more.

The layers are not limited in the thickness thereof, and in the case where a further thinner transistor is demanded, for example, the total thickness of the transistor is preferably from 0.1 to 0.5 μm, and therefor the thickness of the layer is preferably from 10 to 400 nm, and the thickness of the electrode is preferably from 10 to 50 nm.

The material constituting the insulator layer is not particularly limited, as far as the material exhibits insulation effect, and examples thereof include silicon dioxide, silicon nitride, a polyester insulator material, a polycarbonate insulator material, an acrylic polymer insulator material, an epoxy resin insulator material, a polyimide insulator material and a poly-p-xylene insulator material. The upper surface of the insulator layer 13 may be surface-treated, and for example, an insulator layer formed of silicon dioxide that is surface-treated by coating hexamethyldisilazane (HMDS) or octadecyltrichlorosilane (OTS) is preferably used.

Sealing

The device may be entirely sealed with a metallic sealing case, an inorganic material, such as glass and silicon nitride, a high molecular weight material, such as parylene, a low molecular weight material, or the like, for shielding the device from the air and water to enhance the storing stability of the device.

EXAMPLES

The features of the invention will be described more specifically with reference to examples and comparative examples below. The materials, the amounts, the ratios, the contents of process, the procedures of process, and the like shown in the examples may be appropriately changed unless the substance of the invention is deviated. Therefore, the scope of the invention is not construed as being limited to the specific examples shown below.

Synthesis Example

The compounds 1 to 22 were synthesized by referring to Molecular Electronics and Bioelectronics, The Japan Society of Applied Physics, vol. 22, pp. 9-12 (2011), WO 2009/148016, and the like.

Synthesis Example 1

Synthesis of Compound 1

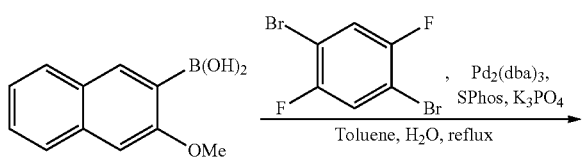

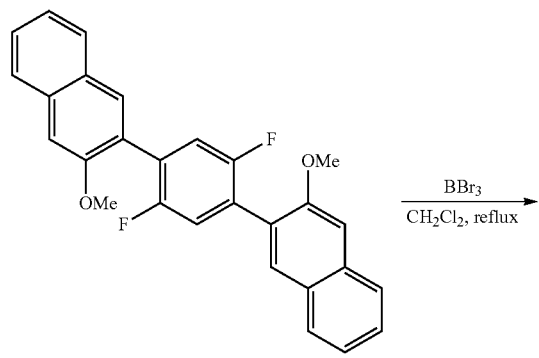

Synthetic intermediate A
yield: 98%

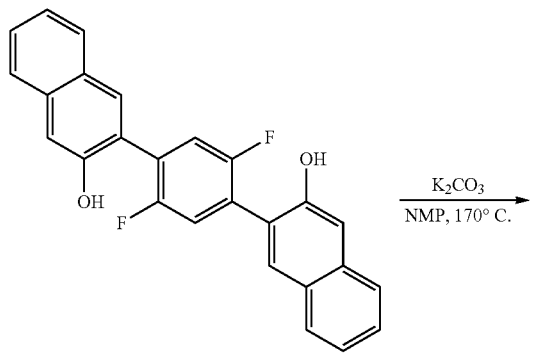

Synthetic intermediate B
yield: 86%

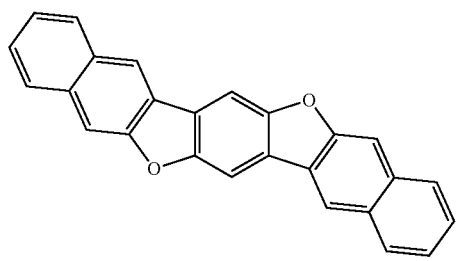

Compound 1
yield: 87%

A synthetic intermediate B was synthesized according to the aforementioned synthetic route. 1.99 g (5.00 mmol) of the synthetic intermediate B, 1.66 g (12.0 mmol) of potassium carbonate and 30 mL of dehydrated N-methylpyrrolidone (NMP) were mixed and stirred under a nitrogen atmosphere at 170° C. for 1.5 hours. After cooling the reaction liquid to room temperature, the solid content was collected therefrom by filtration and then rinsed with NMP, pure water and acetone in this order. The resulting powder was rinsed with flowing ethyl acetate to provide 2.43 g of the compound 1 as pale yellow powder (yield: 87%).

$^1$H NMR Data of Compound 1

$^1$H NMR (400 MHz, in THF-$d_8$, cumulative number: 5,000); δ=8.66 (s, 2H), 8.36 (s, 2H), 8.09 (d, 2H), 8.02-8.00 (m, 4H), 7.54-7.46 (m, 4H) ppm The compounds 2 to 22 were synthesized in the similar manner.

$^1$H NMR Data of Compound 22

Figure 2:
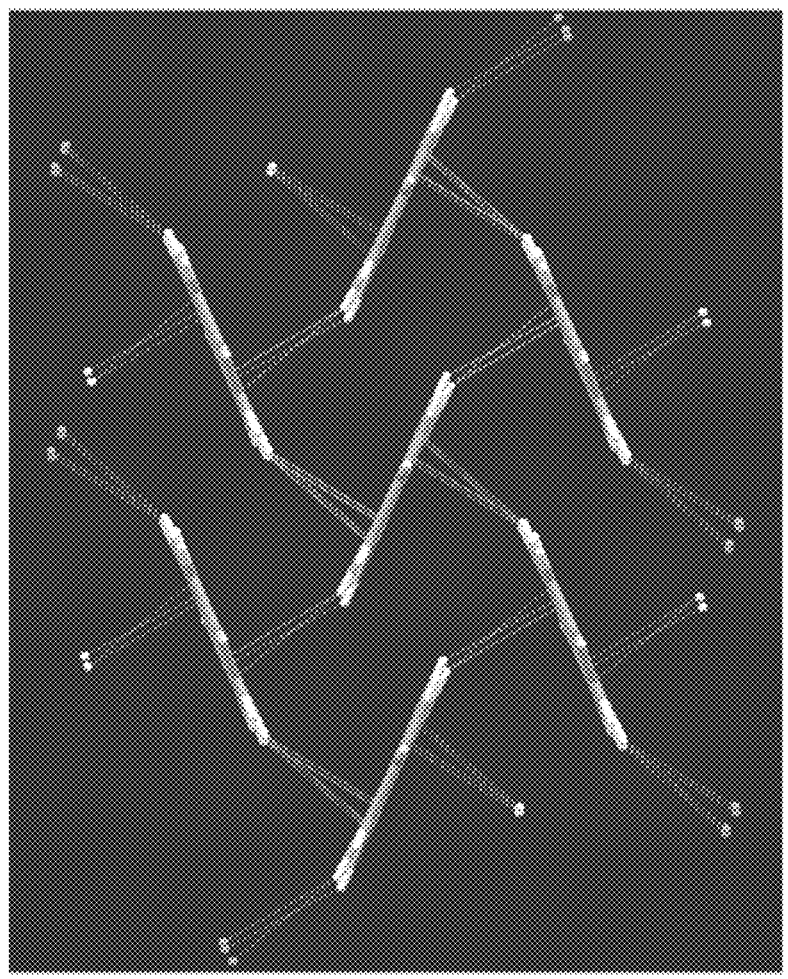
FIG. 2 is an example of a diagram of X-ray structure analysis of a single crystal of the compound 1 showing the molecular packing structure in the example.

$^1$H NMR (400 MHz, in CDCl$_3$); δ=8.49 (s, 1H), 8.19 (s, 1H), 8.08-8.04 (m, 3H), 7.99 (d, 1H), 7.94 (s, 1H), 7.63 (d, 1H), 7.56-7.48 (m, 3H), 7.40 (t, 1H) ppm Evaluation of Properties of Material The crystal of the compound 1 after sublimation purification was subjected to single crystal X-ray structure analysis, and the resulting molecular packing structure is shown in FIG. 2. It was found from FIG. 2 that the compound 1 showed a herringbone packing structure.

Production and Evaluation of Device

The materials used for producing a device were purified by sublimation, and it was confirmed that the materials had a purity of 99.5% or more with high performance liquid chromatography (Tosoh TSKgel ODS-100Z) (purity: area ratio of absorption intensity at 254 nm).

Example 1

Formation of Organic Semiconductor Layer Only with Compound

Figure 3:
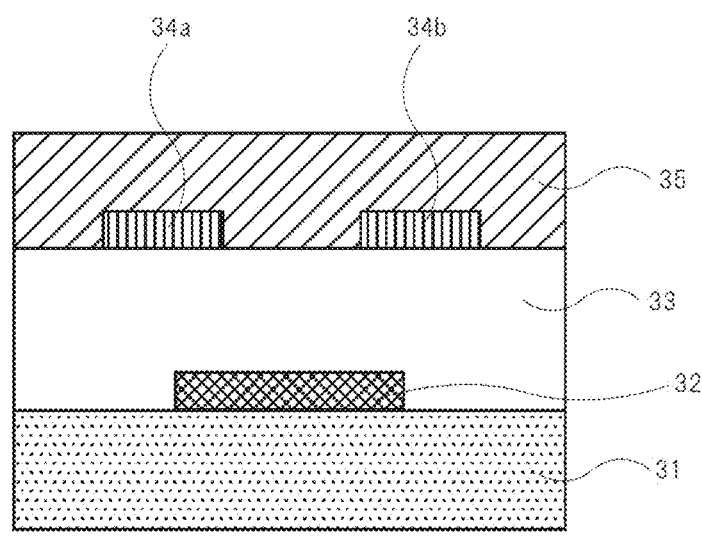
FIG. 3 is an illustration showing an FET characteristics measuring substrate used in the invention.

The compound of the invention or a comparative compound (1 mg) and 1,2-dichlorobenzene (1 mL) were mixed and heated to 100° C. The resulting solution was cast on an FET characteristics measuring substrate heated to 100° C. under a nitrogen atmosphere to provide an FET characteristics measuring device. The FET characteristics measuring substrate used was one shown in FIG. 3, which was a silicon substrate having a bottom-contact structure having source and drain electrodes formed of chromium-gold disposed in an interdigitated layout (gate width W=100,000 μm, gate length L=100 μm) and an insulator film formed of SiO$_2$ (thickness: 200 nm). The FET characteristics were evaluated for the carrier mobility, the change in the mobility after heating the device, and the change in the threshold voltage after high voltage operation, under a nitrogen atmosphere at an atmospheric pressure by using a semiconductor parameter analyzer (4156C, available from Agilent Technologies, Inc.) having a semiautomatic prober (AX-2000, available from Vector Semiconductor Co., Ltd.). The results obtained are shown in Table 1 below.

(a) Carrier Mobility

While applying a voltage of −100 V between the source electrode and the drain electrode of the FET device, the gate voltage was changed within a range of from 20 to −100 V, and the carrier mobility μ was calculated from the following expression showing the drain current $I_d$.

$$I_d = (w/2L)\mu C_i(V_g - V_{th})^2$$

wherein L represents the gate length, W represents the gate width, $C_i$ represents the capacity of the insulator layer per unit area, $V_g$ represents the gate voltage, and $V_{th}$ represents the threshold voltage. A device that had a carrier mobility of less than 1×10$^{-5}$ cm$^2$/Vs was not subjected to the subsequent evaluation for the items (b) and (c) below since the characteristics thereof were too deteriorated.

(b) Change in Mobility after Heating in Air

After heating the device to 120° C. for one hour in the air, the device was measured for the carrier mobility in the same manner as in the item (a), and the ratio ($\mu_1/\mu_0$) of the mobility before storing $\mu_0$ and the mobility after storing $\mu_1$ was evaluated by the following three grades. A larger value therefor means higher thermal stability of the device in the air and thus is preferred.

| | |
|---|---|
| $\mu_1/\mu_0 \geq 0.5$ | A: |
| $0.1 \leq \mu_1/\mu_0 < 0.5$ | B: |
| $\mu_1/\mu_0 < 0.1$ | C: |

(c) Change in Threshold Voltage after Repeated Operation

While applying a voltage of −100 V between the source electrode and the drain electrode and changing the gate voltage repeatedly 100 times within a range of from 20 to −100 V, the same measurement as in the item (a) was performed, and the difference ($|V_1-V_0|$) between the threshold voltage before repeated operation $V_0$ and the threshold voltage after repeated operation $V_1$ was evaluated by the following three grades. A smaller value therefor means higher stability of the device in repeated operation and thus is preferred.

| | |
|---|---|
| $|V_1-V_0| \leq 5$ V | A: |
| $5$ V $\leq |V_1-V_0| < 10$ V | B: |
| $|V_1-V_0| > 10$ V | C: |

The compounds 1 to 22 used as the organic semiconductor material in Table 1 below had the following structures.

Compound 1

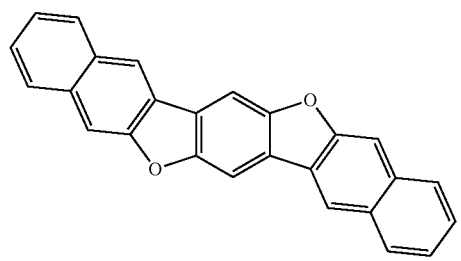

Compound 2

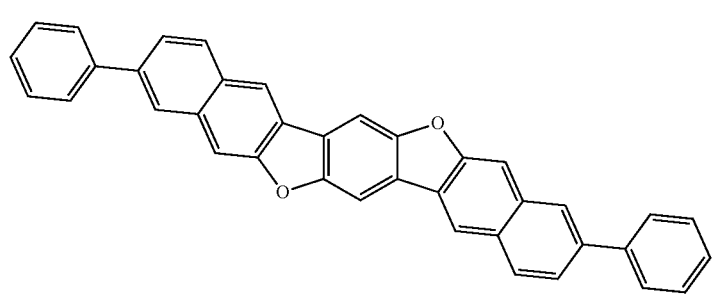

Compound 3

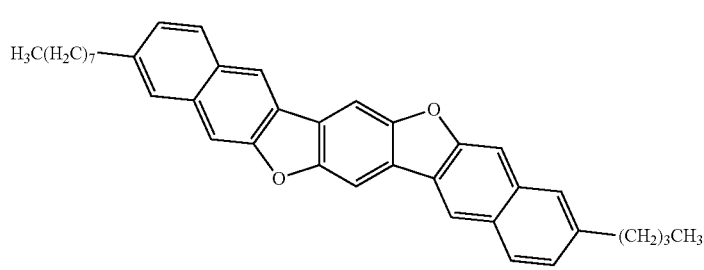

Compound 4

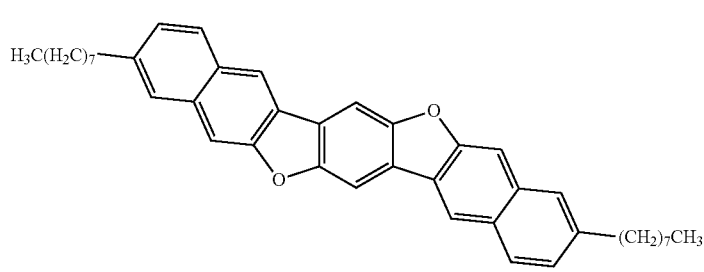

-continued
Compound 5
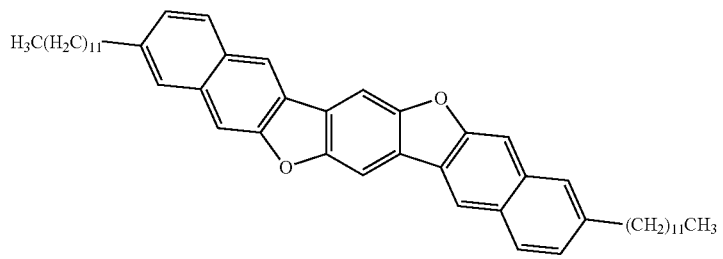
Compound 6
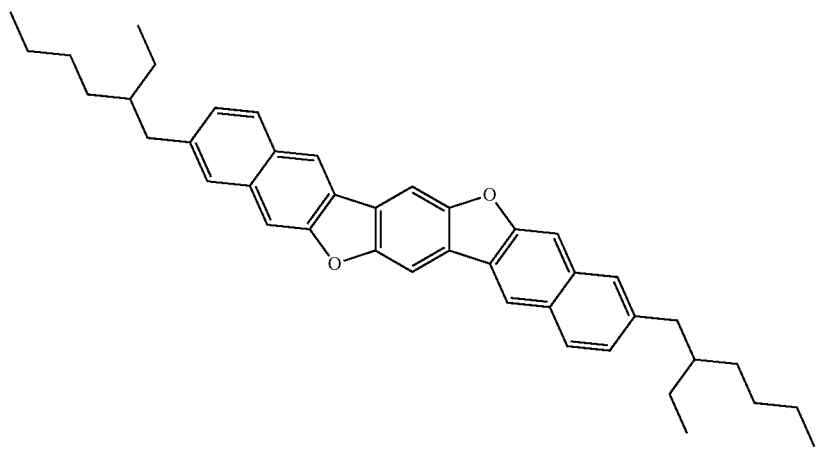
Compound 7
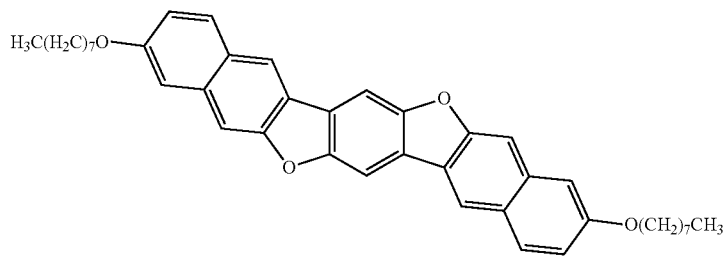
Compound 8
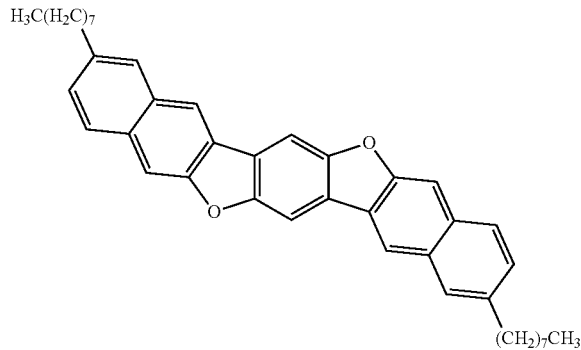

-continued
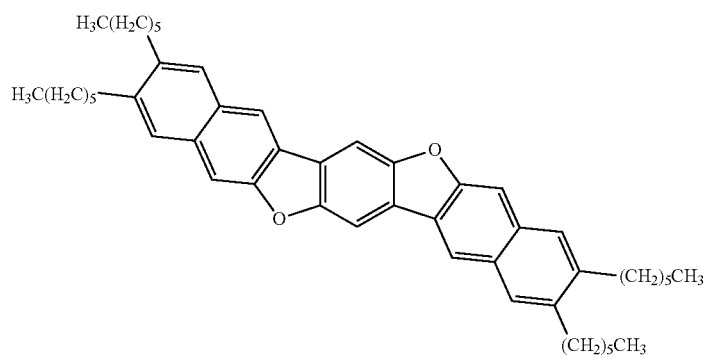
Compound 9
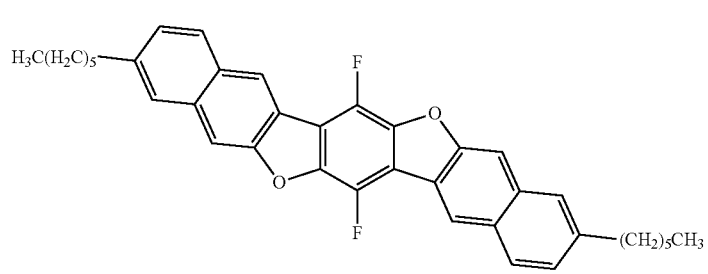
Compound 10
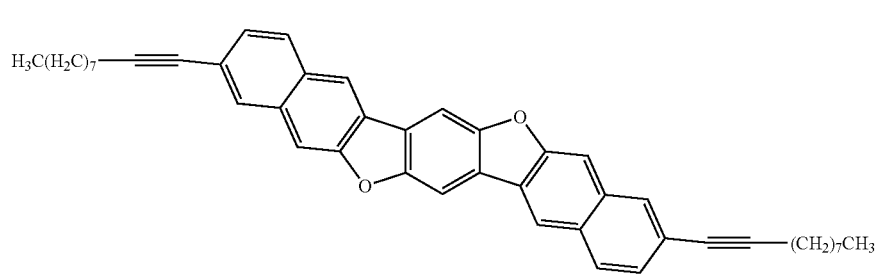
Compound 11
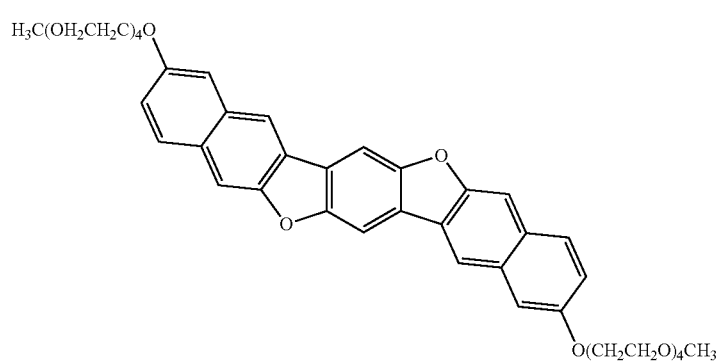
Compound 12

Compound 13
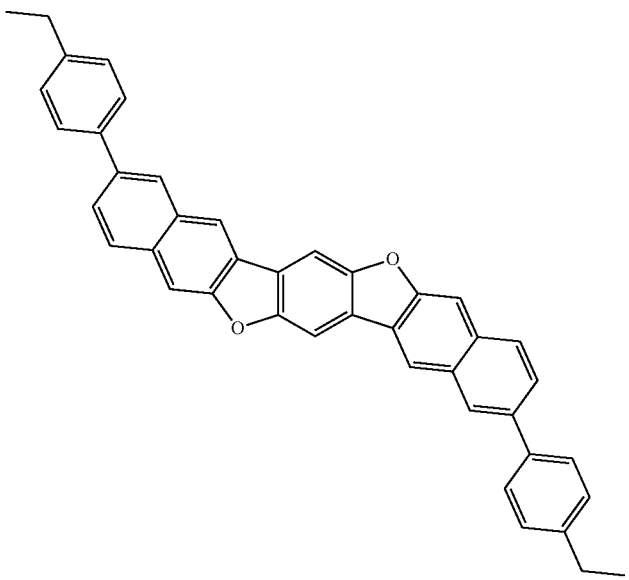
Compound 14
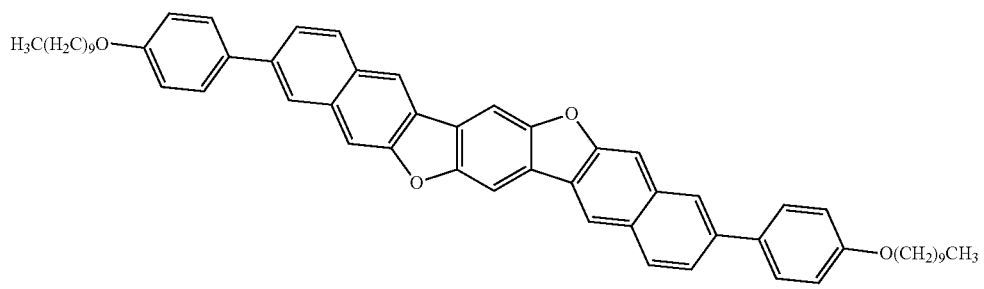
Compound 15
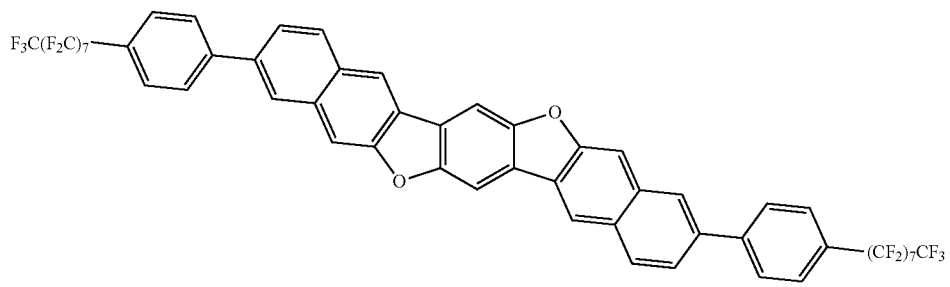
Compound 16
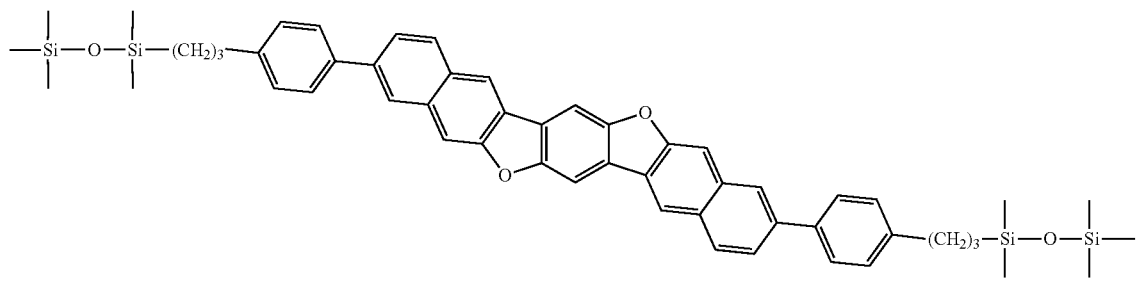

-continued
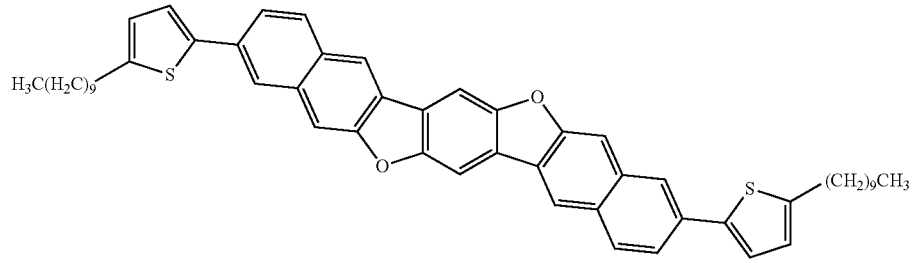
Compound 17
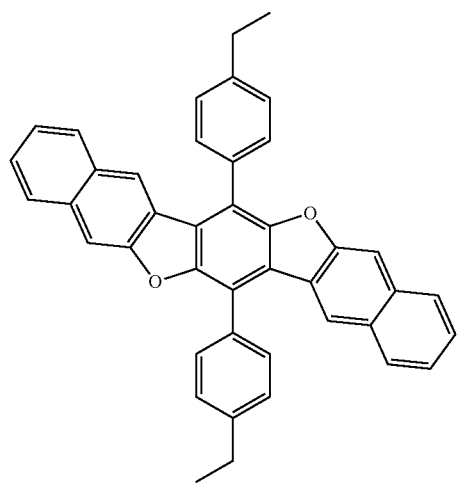
Compound 18
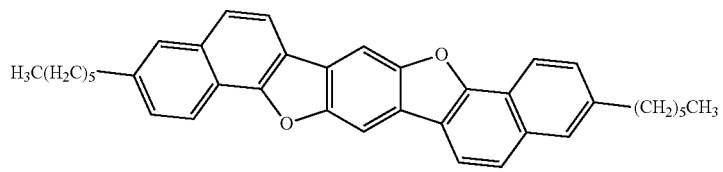
Compound 19
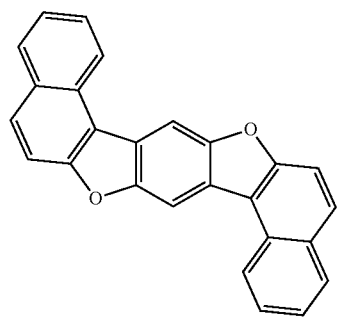
Compound 20
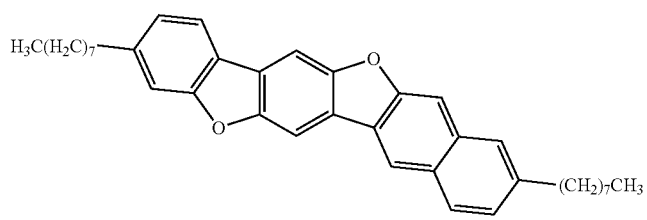
Compound 21

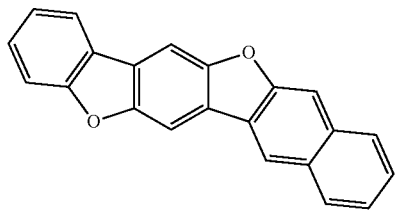
The comparative compounds 1 to 10 used as a comparative organic semiconductor material in Table 1 below had the following structures.
Comparative Compound 1
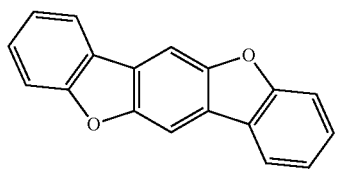
Comparative Compound 2
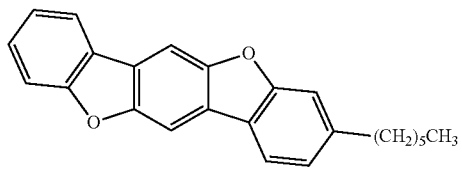
Comperative Compound 3
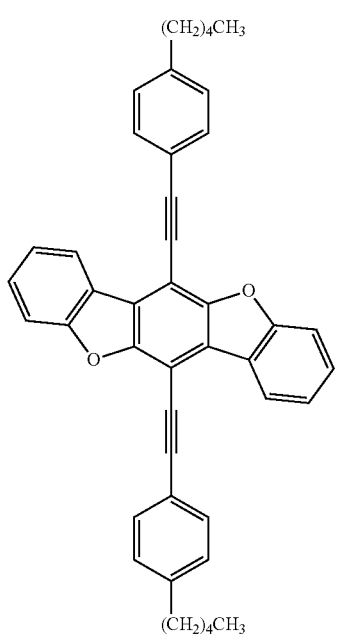
Compound 22
-continued
Comperative Compound 4
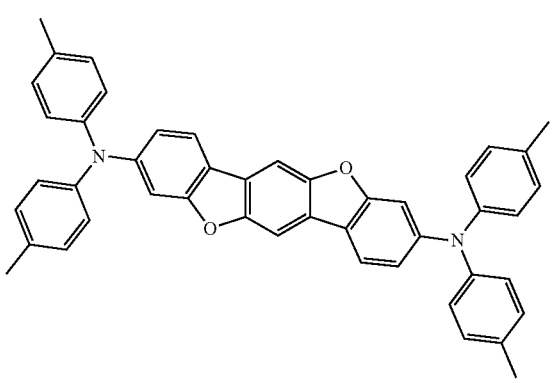
Comparetive Compound 5
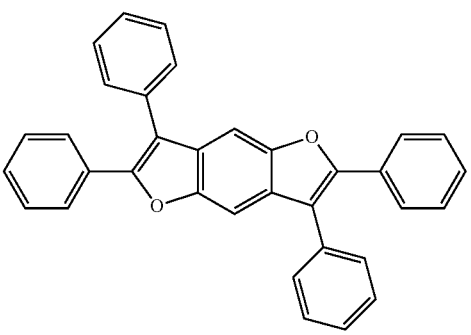
Comperative Compound 6
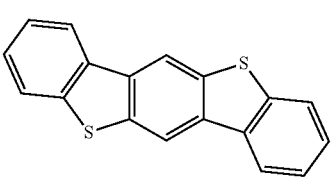

-continued

Comperative Compound 7

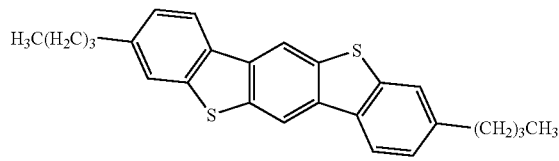

Comperative Compound 8

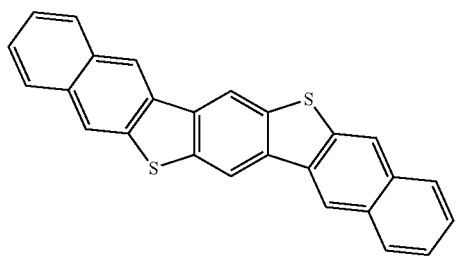

Comperative Compound 9

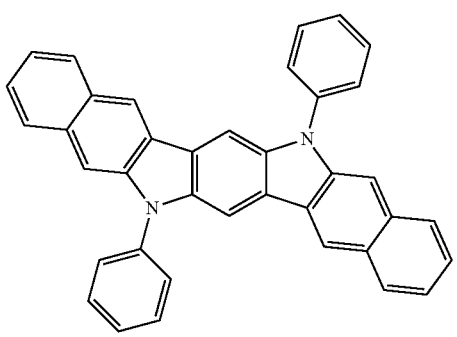

Comperative Compound 10

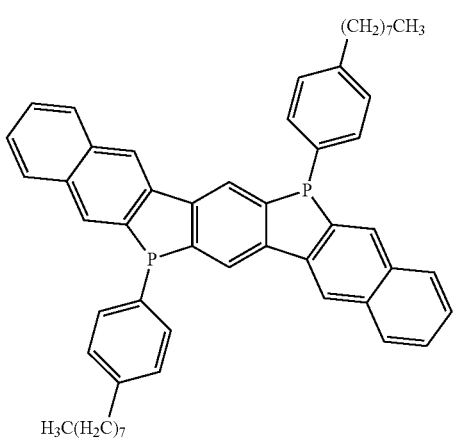

TABLE 1

| Device No. | Organic semiconductor material | Carrier mobility (cm$^2$/Vs) | Change in mobility after heating | Change in threshold voltage after repeated operation | Note |
|---|---|---|---|---|---|
| Device 1 | Compound 3 | $2 \times 10^{-2}$ | A | A | invention |
| Device 2 | Compound 4 | $9 \times 10^{-2}$ | A | A | invention |
| Device 3 | Compound 5 | $8 \times 10^{-2}$ | A | A | invention |
| Device 4 | Compound 6 | $1 \times 10^{-2}$ | A | A | invention |
| Device 5 | Compound 7 | $5 \times 10^{-2}$ | A | A | invention |
| Device 6 | Compound 8 | $3 \times 10^{-2}$ | A | A | invention |
| Device 7 | Compound 10 | $2 \times 10^{-2}$ | A | A | invention |
| Device 8 | Compound 11 | $1 \times 10^{-2}$ | A | A | invention |
| Device 9 | Compound 12 | $6 \times 10^{-3}$ | A | A | invention |
| Device 10 | Compound 14 | $1 \times 10^{-2}$ | A | A | invention |
| Device 11 | Compound 15 | $1 \times 10^{-2}$ | A | A | invention |
| Device 12 | Compound 16 | $8 \times 10^{-3}$ | A | A | invention |
| Device 13 | Compound 17 | $2 \times 10^{-2}$ | A | A | invention |
| Device 14 | Compound 19 | $9 \times 10^{-3}$ | A | A | invention |
| Device 15 | Compound 21 | $1 \times 10^{-2}$ | B | A | invention |
| Comparative Device 1 | Comparative Compound 1 | $<1 \times 10^{-5}$ | — | — | comparison |
| Comparative Device 2 | Comparative Compound 2 | $1 \times 10^{-3}$ | C | C | comparison |
| Comparative Device 3 | Comparative Compound 3 | $<1 \times 10^{-5}$ | — | — | comparison |
| Comparative Device 4 | Comparative Compound 4 | $<1 \times 10^{-5}$ | — | — | comparison |
| Comparative Device 5 | Comparative Compound 5 | $<1 \times 10^{-5}$ | — | — | comparison |
| Comparative Device 6 | Comparative Compound 6 | $2 \times 10^{-4}$ | B | C | comparison |
| Comparative Device 7 | Comparative Compound 7 | $5 \times 10^{-5}$ | B | C | comparison |
| Comparative Device 8 | Comparative Compound 8 | $<1 \times 10^{-5}$ | — | — | comparison |

TABLE 1-continued

| Device No. | Organic semiconductor material | Carrier mobility ($cm^2/Vs$) | Change in mobility after heating | Change in threshold voltage after repeated operation | Note |
|---|---|---|---|---|---|
| Comparative Device 9 | Comparative Compound 9 | $<1 \times 10^{-5}$ | — | — | comparison |
| Comparative Device 10 | Comparative Compound 10 | $<1 \times 10^{-5}$ | — | — | comparison |

Example 2

Formation of Organic Semiconductor Layer with Binder

An FET characteristics measuring device was produced in the same manner as in Example 1 except that the coating liquid used was a solution obtained in such a manner that the compound of the invention or a comparative compound (0.5 mg), PaMS (poly(α-methylstyrene), produced by Sigma-Aldrich Corporation) and 1,2-dichlorobenzene (1 mL) were mixed and heated to 100° C., and evaluated in the same manner as in Example 1. The results obtained are shown in Table 2 below.

TABLE 2

| Device No. | Organic semiconductor material | Carrier mobility ($cm^2/Vs$) | Change in mobility after heating | Change in threshold voltage after repeated operation | Note |
|---|---|---|---|---|---|
| Device 16 | Compound 1 | $8 \times 10^{-3}$ | A | A | invention |
| Device 17 | Compound 2 | $7 \times 10^{-3}$ | A | A | invention |
| Device 18 | Compound 4 | $1 \times 10^{-2}$ | A | A | invention |
| Device 19 | Compound 9 | $1 \times 10^{-3}$ | A | A | invention |
| Device 20 | Compound 13 | $9 \times 10^{-3}$ | A | A | invention |
| Device 21 | Compound 18 | $2 \times 10^{-3}$ | A | A | invention |
| Device 22 | Compound 20 | $3 \times 10^{-3}$ | A | A | invention |
| Comparative Device 11 | Comparative Compound 2 | $7 \times 10^{-5}$ | B | C | comparison |
| Comparative Device 12 | Comparative Compound 6 | $<1 \times 10^{-5}$ | — | — | comparison |
| Comparative Device 13 | Comparative Compound 7 | $<1 \times 10^{-5}$ | — | — | comparison |
| Comparative Device 14 | Comparative Compound 8 | $<1 \times 10$-5 | — | — | comparison |
| Comparative Device 15 | Comparative Compound 9 | $<1 \times 10^{-5}$ | — | — | comparison |

As a result of the observation with an optical microscope and an atomic force microscope (AFM), it was found that all the thin films using PaMS as a binder had considerably high smoothness and uniformity of the film. As a result of the comparison between the device 2 and the device 17, the device 17 was higher in smoothness and uniformity of the film. It was understood therefrom that the comparative devices exhibited an extremely low carrier mobility in the composite system with the binder, but the compound of the invention provided such devices that exhibited a good carrier mobility even using with a binder, a small change in the mobility after heating, a small change in the threshold voltage after repeated operation, and considerably high smoothness and uniformity of the film.

It was understood from the results in Tables 1 and 2 that the organic thin film transistor using the compound of the invention had a high carrier mobility, a small change in the mobility after heating, and a small change in the threshold voltage after repeated operation.

On the other hand, it was found that the comparative compounds 1 to 10 failing to satisfy the requirement of the compound of the invention had a low carrier mobility. It was found that in particular the comparative compounds 1, 3 to 5 and 8 to 10 had an extremely low carrier mobility. It was found that the comparative compounds 2, 6 and 7 had a large change in the mobility after heating and a large change in the threshold voltage after repeated operation.

The comparative compounds 1 and 2 are the compounds described in Molecular Electronics and Bioelectronics, The Japan Society of Applied Physics, vol. 22, pp. 9-12 (2011), the comparative compound 3 is the compound described in JP-A-2007-88222, the comparative compound 4 is the compound described in WO 2006/122630, the comparative compound 5 is the compound described in US 2012/0074396, the comparative compounds 6, 8 and 10 are the compounds described in JP-A-2008-81494, the comparative compounds 6 and 7 are the compounds described in J. Am. Chem. Soc., vol. 132, pp. 11702-11708 (2010), and the comparative compound 9 is the compound described in WO 2010/107244.

As a result of the visual observation and the observation with an optical microscope, it was found that the thin film using PaMS as a binder had considerably high smoothness and uniformity of the film. As a result of the comparison between the device 2 and the device 18, the device 18 was higher in smoothness and uniformity of the film. It was understood therefrom that the comparative devices exhibited an extremely low carrier mobility in the composite system with the binder, but the compound of the invention provided such devices that exhibited a good carrier mobility even using with a binder, a small change in the mobility after heating, a small change in the threshold voltage after repeated operation, and considerably high smoothness and uniformity of the film.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/071323, filed Aug. 7, 2013, and Japanese Patent Application No. 2012-187059 filed on Aug. 27, 2012, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

REFERENCE SIGNS LIST 11 substrate
12 electrode
13 insulator layer
14 organic material layer (semiconductor active layer)
15a, 15b electrode
31 substrate
32 electrode
33 insulator layer
34a, 34b electrode
35 organic material layer (semiconductor active layer)

What is claimed is:

1. An organic thin film transistor having a semiconductor active layer containing a compound represented by the following general formula (2):

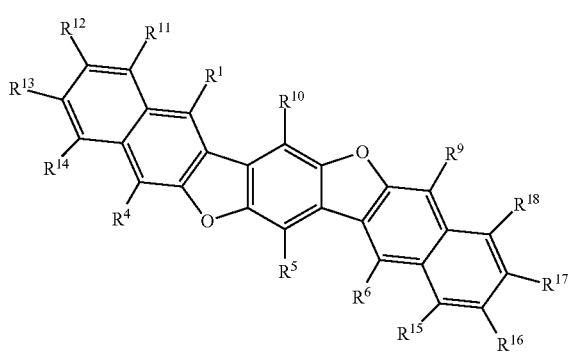

General Formula (2)

wherein in the general formula (2), $R^1$, $R^4$ to $R^6$ and $R^9$ to $R^{18}$ each independently represents a hydrogen atom or a substituent.

2. The organic thin film transistor according to claim 1, wherein at least one of $R^1$, $R^4$ to $R^6$ and $R^9$ to $R^{18}$ represents a substituent represented by the following general formula (W):

*-L-R  General Formula (W)

wherein in the general formula (W), a position shown by * represents a bonding position to the benzobisnaphthofuran skeleton; L represents a single bond or a divalent linking group; and R represents an alkyl group having 2 or more carbon atoms, an oligoethyleneoxy group having a number of repetition of ethyleneoxy units of 2 or more, or an oligosiloxane group having 2 or more silicon atoms.

3. The organic thin film transistor according to claim 1, wherein the compound represented by the general formula (2) is represented by the following general formula (3-1) or (3-2):

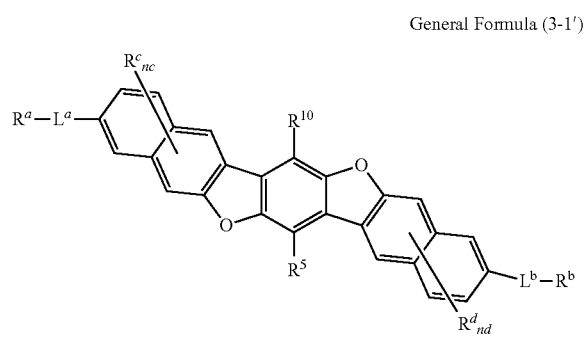

General Formula (3-1')

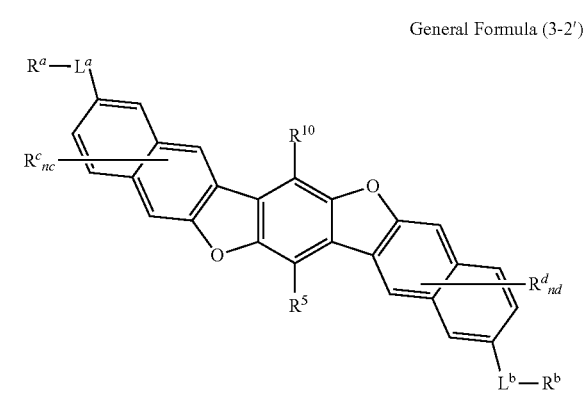

General Formula (3-2')

wherein in the general formulae (3-1) and (3-2), $R^5$ and $R^{10}$ each independently represents a hydrogen atom or a substituent; $L^a$ and $L^b$ each independently represents a single bond or a divalent linking group; $R^a$ and $R^b$ each independently represents an alkyl group having 2 or more carbon atoms, an oligoethyleneoxy group having a number of repetition of ethyleneoxy units of 2 or more, or an oligosiloxane group having 2 or more silicon atoms; $R^c$ and $R^d$ each independently represents a substituent; and nc and nd each independently represents an integer of from 0 to 5.

4. The organic thin film transistor according to claim 3, wherein in the general formula (3-1) or the general formula (3-2), $L^a$ and $L^b$ each are selected from a single bond and the following general formulae (L-1) to (L-12):

$$\{-(CR'_2)_n-*\quad\text{(L-1)}$$

-continued

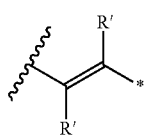
(L-2)

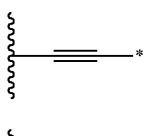
(L-3)

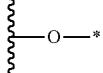
(L-4)

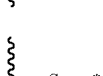
(L-5)

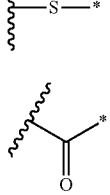
(L-6)

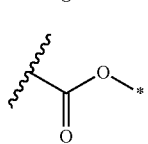
(L-7)

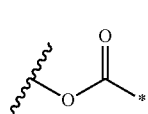
(L-8)

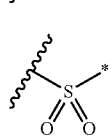
(L-9)

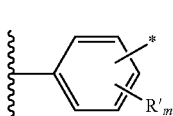
(L-10)

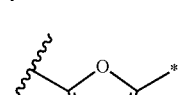
(L-11)

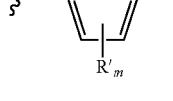
(L-12)

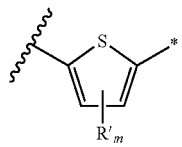

wherein in the general formulae (L-1) to (L-12), a position shown by a wave line represents a bonding position to the benzobisnaphthofuran skeleton; a position shown by * represents the bonding position to R in the general formula (W); n in the general formula (L-1) represents an integer of 1 or more; m in the general formula (L-10) represents 4; m in the general formulae (L-11) and (L-12) represents 2; and R' in the general formulae (L-1), (L-2), (L-10), (L-11) and (L-12) each independently represents a hydrogen atom or a substituent.

5. The organic thin film transistor according to claim 3, wherein in the general formula (3-1) or the general formula (3-2), both $L^a$ and $L^b$ each are a single bond.

6. The organic thin film transistor according to claim 3, wherein in the general formula (3-1) or the general formula (3-2), all $R^a$, $R^b$, $R^c$ and $R^d$ each are an alkyl group.

7. The organic thin film transistor according to claim 3, wherein in the general formula (3-1) or the general formula (3-2), all $R^a$, $R^b$, $R^c$ and $R^d$ each are an alkyl group having from 6 to 12 carbon atoms.

8. A compound represented by the following general formula (2'):

General Formula (2')

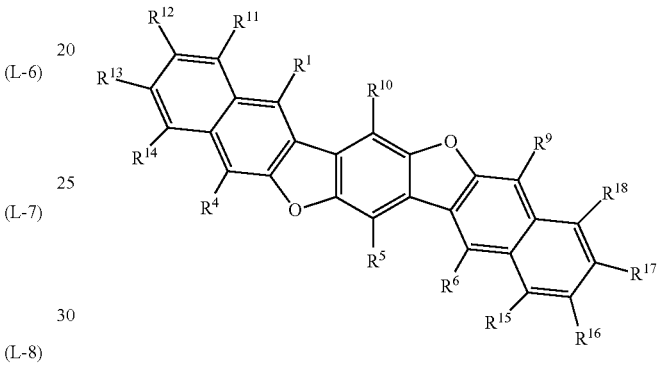

wherein in the general formula (2'), $R^1$, $R^4$ to $R^6$ and $R^9$ to $R^{18}$ each independently represents a hydrogen atom or a substituent, provided that at least one of $R^1$, $R^4$ to $R^6$ and $R^9$ to $R^{18}$ represents a substituent.

9. The compound according to claim 8, wherein the compound represented by the general formula (2') is represented by the following general formula (3-1') or (3-2'):

General Formula (3-1')

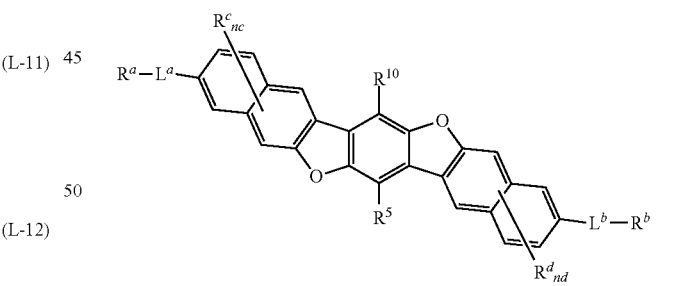

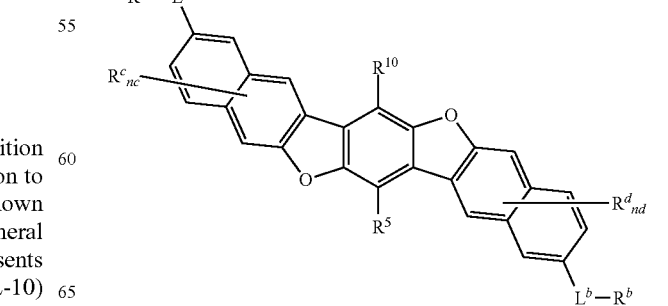

wherein in the general formulae (3-1') and (3-2'), $R^5$ and $R^{10}$ each independently represents a hydrogen atom or a substituent; $L^a$ and $L^b$ each independently represents a single bond or a divalent linking group; $R^a$ and $R^b$ each independently represents an alkyl group having 2 or more carbon atoms, an oligoethyleneoxy group having a number of repetition of 2 or more, or an oligosiloxane group having a number of repetition of 2 or more; $R^c$ and $R^d$ each independently represents a substituent; and nc and nd each independently represents an integer of from 0 to 5.

10. An organic semiconductor material for a non-light-emitting organic semiconductor device, containing a compound represented by the following general formula (2):

General Formula (2)

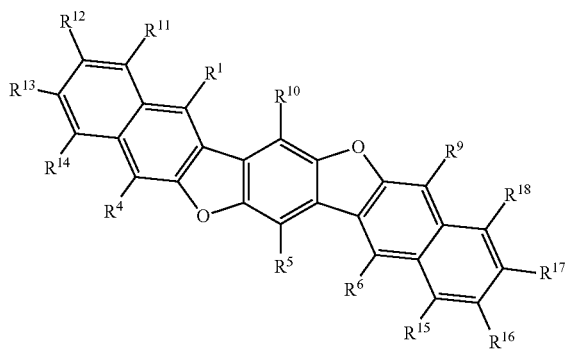

wherein in the general formula (2), $R^1$, $R^4$ to $R^6$ and $R^9$ to $R^{18}$ each independently represents a hydrogen atom or a substituent.

11. A material for an organic thin film transistor, containing a compound represented by the following general formula (2):

General Formula (2)

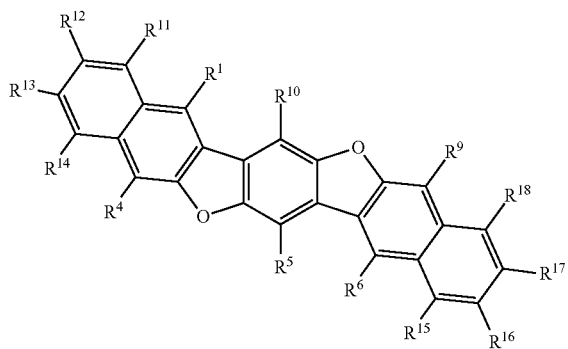

wherein in the general formula (2), $R^1$, $R^4$ to $R^6$ and $R^9$ to $R^{18}$ each independently represents a hydrogen atom or a substituent.

12. A coating solution for a non-light-emitting organic semiconductor device, containing a compound represented by the following general formula (2):

General Formula (2)

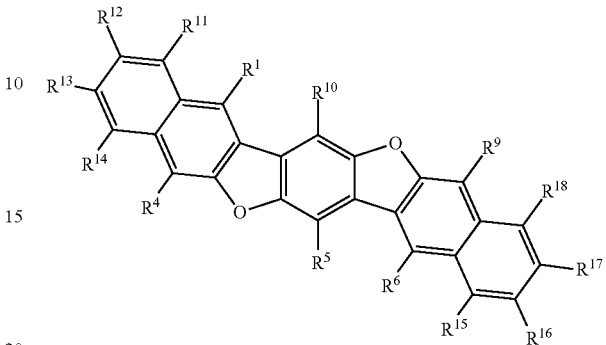

wherein in the general formula (2), $R^1$, $R^4$ to $R^6$ and $R^9$ to $R^{18}$ each independently represents a hydrogen atom or a substituent.

13. The coating solution for a non-light-emitting organic semiconductor according to claim 12, which further contains a polymer binder.

14. An organic semiconductor thin film containing the coating solution having been coated and dried, wherein the coating solution contains a compound represented by the following general formula (2):

General Formula (2)

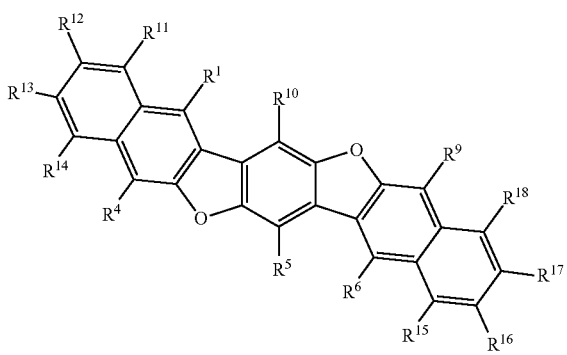

wherein in the general formula (2), $R^1$, $R^4$ to $R^6$ and $R^9$ to $R^{18}$ each independently represents a hydrogen atom or a substituent.

15. The organic semiconductor thin film according to claim 14 wherein the coating solution further contains a polymer binder.

* * * * *